(12) United States Patent
Bond et al.

(10) Patent No.: US 7,091,338 B2
(45) Date of Patent: Aug. 15, 2006

(54) PURIFICATION OF 4,4'(5')-DI-T-BUTYLCYCLOHEXANO-18-CROWN-6

(75) Inventors: Andrew H. Bond, Hoffman Estates, IL (US); Richard E. Barrans, Jr., Downers Grove, IL (US); E. Philip Horwitz, Naperville, IL (US)

(73) Assignee: PG Research Foundation, Darien, IL (US)

( * ) Notice: Subject to any disclaimer, the term of this patent is extended or adjusted under 35 U.S.C. 154(b) by 285 days.

(21) Appl. No.: 10/284,968

(22) Filed: Oct. 31, 2002

(65) Prior Publication Data

US 2003/0105375 A1    Jun. 5, 2003

Related U.S. Application Data

(60) Provisional application No. 60/335,991, filed on Nov. 15, 2001.

(51) Int. Cl.
*C07B 47/00* (2006.01)
*C07D 321/12* (2006.01)
*C07C 321/00* (2006.01)
*B01D 15/08* (2006.01)
*B01D 39/00* (2006.01)

(52) U.S. Cl. .............. 540/145; 540/469; 549/349; 564/512; 566/57; 566/606; 210/198.2; 210/502.1

(58) Field of Classification Search .............. 549/549, 549/349; 210/198.2–502.1; 540/145, 469; 568/57, 60.6; 564/512
See application file for complete search history.

(56) References Cited

U.S. PATENT DOCUMENTS

| | | | |
|---|---|---|---|
| 5,100,585 A | 3/1992 | Horwitz et al. |
| 5,110,474 A | 5/1992 | Horwitz et al. |
| 5,344,623 A | 9/1994 | Horwitz et al. |
| 5,346,618 A | 9/1994 | Horwitz et al. |
| 5,478,953 A | 12/1995 | Gula et al. |
| 6,075,130 A | 6/2000 | Chen et al. |
| 6,174,503 B1 | 1/2001 | Moyer et al. |
| 6,297,395 B1 | 10/2001 | Nicholsen et al. |

(Continued)

FOREIGN PATENT DOCUMENTS

EP    0 000 219 A1    1/1979

(Continued)

OTHER PUBLICATIONS

Curran, Angew. Chem. Int. Ed. vol. 37 pp. 1174-1196 (1998) "Strategy-Level Separations in Organic Synthesis".*

(Continued)

*Primary Examiner*—Cecilia J. Tsang
*Assistant Examiner*—Raymond Covington
(74) *Attorney, Agent, or Firm*—Welsh & Katz, Ltd.

(57) ABSTRACT

A purification method is disclosed for a predetermined water-insoluble extractant present in a liquid phase composition that additionally contains one or more additional extractants, synthesis reaction starting materials, and reaction byproducts dissolved as solutes in an organic diluent. An ion-containing compound is admixed with the composition to form an extractant/ion complex in the organic diluent phase that has an affinity for a new phase that is greater than the affinity for the first-named phase. The predetermined extractant/ion complex is separated from the diluent by using the new phase affinity, and the extractant/ion complex is preferably although not necessarily recovered. The extractant/ion complex is separated into extractant and ion. The extractant is recovered. Exemplary extractants include polyethers, crown ethers, crown thioethers, calixarenes, polyamines, cryptands, porphyrins and the like.

28 Claims, 22 Drawing Sheets

U.S. PATENT DOCUMENTS 6,322,702 B1  11/2001  Moyer et al.
6,326,394 B1  12/2001  Schmitt et al.

FOREIGN PATENT DOCUMENTS

EP  0 611 763 A1  8/1994

OTHER PUBLICATIONS

Chiarizia et al, Hydrometallurgy (2003) 5th Inter. Conf. pp. 917.*

Wikipedia (Dec. 2005), Liquid—liquid Extraction Section 8.1 Extraction with Chemical Change.*

Perrin et al, Pure & Appl. Chem. vol. 65 No. 7 pp. 1549-1559 (1993).*

Bond et al., "Synergistic Solvent Extraction of Alkaline Earth Cations by Mixtures of Di-n-octylphosphoric Acid and Stereoisomers of Dicyclohexano-18-crown-6", *Anal. Chem.* (1999) 71:2757-2765.

Bond et al., "Incorporating Size Selectivity into Synergistic Solvent Extraction: A Review of Crown Ether-Containing Systems", *Ind. Eng. Chem. Res.* (2000) 39:3442-3464.

Chiarizia et al., "Small Angle Neutron Scattering Investigation of the Species Formed in the Extraction of Sr(II) by Mixtures of DI-n-Octylphosphoric Acid and Dicyclohexano-18-Crown-6", *Solvent Extraction and Ion Exchange* (2000) 18(3):451-478.

Dietz et al., "Ligand Reorganization Energies as a Basis for the Design of Synergistic Metal Ion Extraction Systems", *Chem. Commun.* (1999) 1177-1178.

Dietz et al., "Isomer Effects in the Extraction of Metal Ions from Acidic Nitrate Media by Dicyclohexano-18-crown-6", *Radiochim. Acta* (1999) 85:119-129.

Dietz et al., "Extraction Chromatography: Progress and Opportunities", *Metal-Ion Separation and Preconcentration: Progress and Opportunities*, vol. 716, Bond et al., Eds., American Chemical Society (Washington, D.C.:1999), pp. 234-250.

Dietz et al., "Comparison of Column Chromatographic and Precipitation Methods for the Purification of a Macrocyclic Polyether Extractant", *Separation Science and Technology* (1999) 34:2943-2956.

Hay et al., "The Effect of Adding Alkyl Groups to Dicyclohexano-18-Crown-6 on the Complexation and Solvent Extraction of Strontium", Report RL3-6-C3-31, Pacific Northwest National Laboratory, Richland, WA (Nov. 1996).

Hay, "A Molecular Mechanics Method for Predicting the Influence of Ligand Structure on Metal Ion Binding Affinity", Chapter 6 in *Metal-ion Separation and Preconcentration: Progress and Opportunities*, Bond et al., Eds., American Chemical Society (Washington, D.C.:1999), pp. 102-113.

Horwitz et al., "Correlation of the Extraction of Strontium Nitrate by a Crown Ether with the Water Content of the Organic Phase", *Solvent Extraction and Ion Exchange* (1990) 8(1):199-208.

Horwitz et al., "Extraction of Strontium from Nitric Acid Solutions Using dicyclohexano-18-Crown-6 and Its Derivatives", *Solvent Extraction and Ion Exchange* (1990) 8(4&5):557-572.

Horwitz et al., "SREX: A New Process for the Extraction and Recovery of Strontium from Acidic Nuclear Waste Streams", *Solvent Extraction and Ion Exchange* (1991) 9(1):1-25.

Horwitz et al., "Separation and Preconcentration of Strontium from Biological, Environmental, and Nuclear Waste Samples by Extraction Chromatography Using a Crown Ether", *Anal. Chem.* (1991) 63:522-525.

Horwitz et al., "A Novel Strontium-Selective Extraction Chromatographic Resin", *Solvent Extraction and Ion Exchange* (1992) 10(2):313-336.

Horwitz et al., "Solvent Extraction in the Treatment of Acidic High-Level Liquid Waste: Where Do We Stand?", Metal-Ion Separation and Preconcentration: Progress and Opportunities, Bond et al., Eds., American Chemical Society, Washington, D.C. (1999) 21-50.

Izatt et al., Facile Separation of the Cis Isomers of Dicyclohexyl-18-crown-6 *Inorg. Chem.* (1975) 14:3132-3133.

Izatt et al., "Thermodynamic and Kinetic Data for Macrocycle Interaction with Cations and Anion", *Chem. Rev.* (1991) 91:1721-2085.

Kertes et al., Solvent Extraction Chemistry of Metals, McKay et al., Eds., MacMillian: Londay (1965) 377.

Lasorkin et al., "Separation of 2,5,8,15,18,21-Hexaoxotricyclo 20.4. 0.0$^{9,14}$ Hexacosane Diastereomers by High-Pressure Liquid Chromatography", *Zh. Anal. Khim.* (1984) 39:1115-1119.

Law et al., "Demonstration of a SREX Flowsheet for the Partitioning of Strontium and Lead from Actual ICPP Sodium-Bearing Waste", INEEL/EXT-97-00832, Idaho National Engineering Laboratory, Idaho Falls, ID (1997).

Rogers et al., Crystal Structure of [Pb(cis-anti-cis-dicyclohexyl-18-crown-6)(OH$_2$)$_2$][ClO$_4$] $_2$, *J. of Chemical Crystallography* (1997) 27(4):263-267.

Simonov et al., *Dokl. Akad. Nauk SSSR* (1983) 272:1129-1133.

Vandegrift, In Science and Technology of Tributyl Phosphage. vol. I: Synthesis, Properties, Reactions, and Analysis, Schultz et al., Eds., CRC Press: Boca Raton, FL (1984).

* cited by examiner 4,4'(5')-DI-t-BUTYLCYCLOHEXANO-18-CROWN-6, DtBuCH18C6

4(z),4'(z)-CIS-SYN-CIS-DI-t-BUTYLCYCLOHEXANO-18-CROWN-6

4(z),5'(e)-CIS-ANTI-CIS-DI-t-BUTYLCYCLOHEXANO-18-CROWN-6

FIG. 2
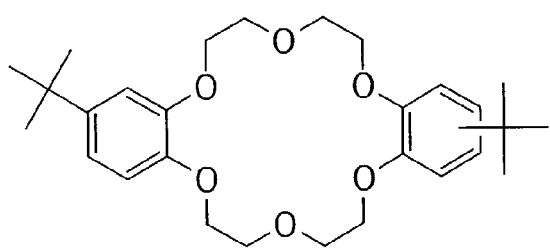
4,4'(5')-DI-t-BUTYLBENZO-18-CROWN-6
DtBuB18C6, RT = 3.0-3.5 MIN.
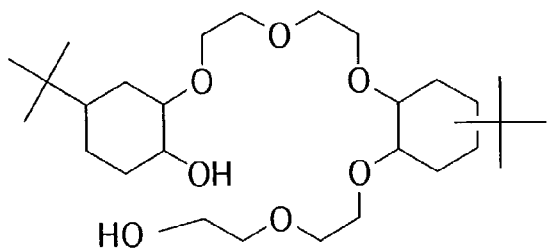
PLUS OTHER CLEAVAGE ISOMERS
ACYCLIC DIOL, RT = 2.5-3.0 MIN.
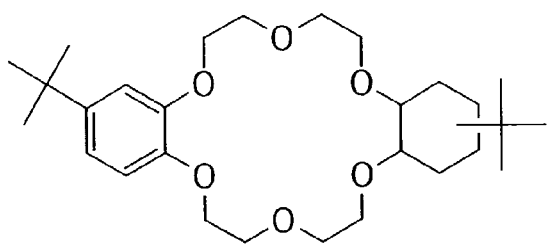
4-t-BUTYLBENZO-4'(5')-t-BUTYLCYCLOHEXANO
-18-CROWN-6
(tBuB)(tBuCH)18C6, RT = 5.5-6.0 MIN.
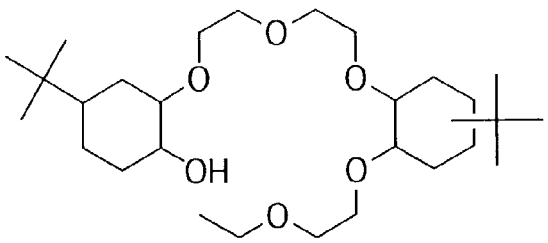
PLUS OTHER CLEAVAGE ISOMERS
ACYCLIC ETHYL ETHER, RT = 5.5-6.0 MIN.
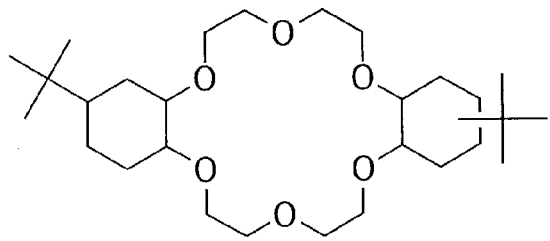
4,4'(5')-DI-t-BUTYLCYCLOHEXANO
-18-CROWN-6
DtBuCH18C6, RT = 7.0-10.0 MIN.
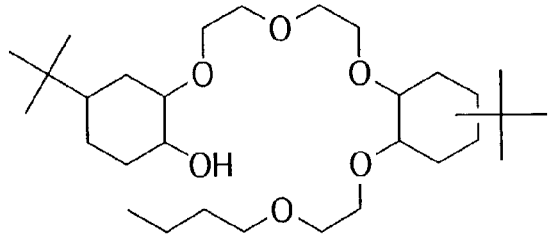
PLUS OTHER CLEAVAGE ISOMERS
ACYCLIC BUTYL ETHER, RT = 10.0-12.0 MIN.

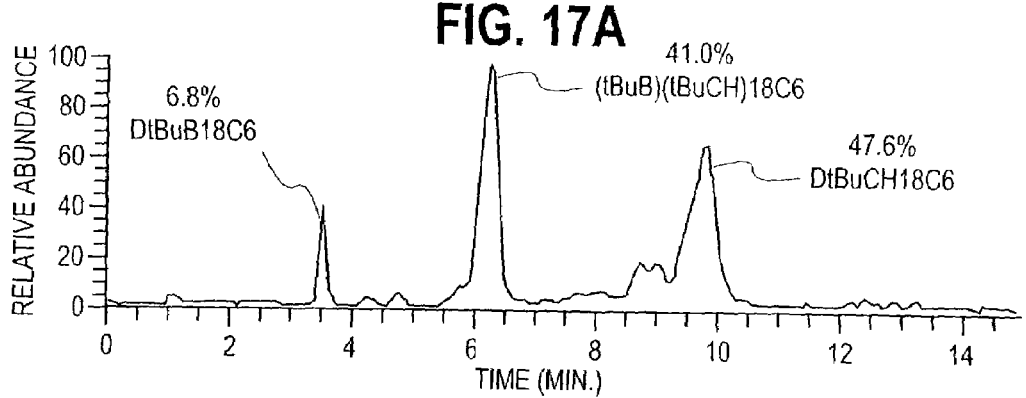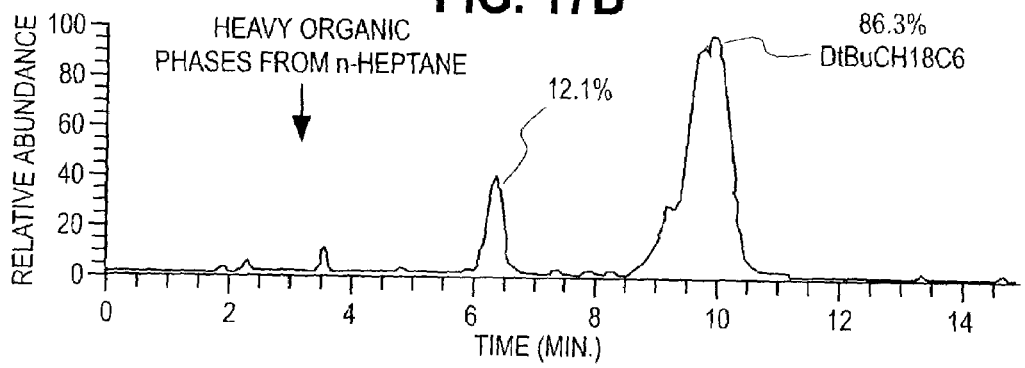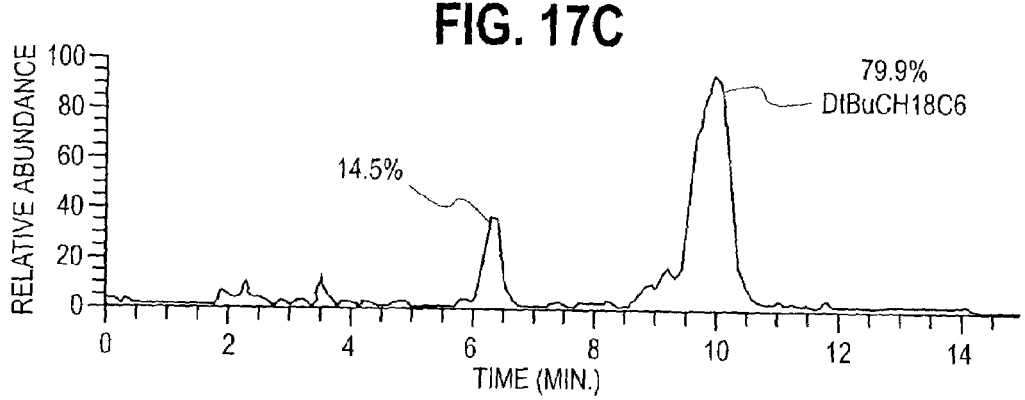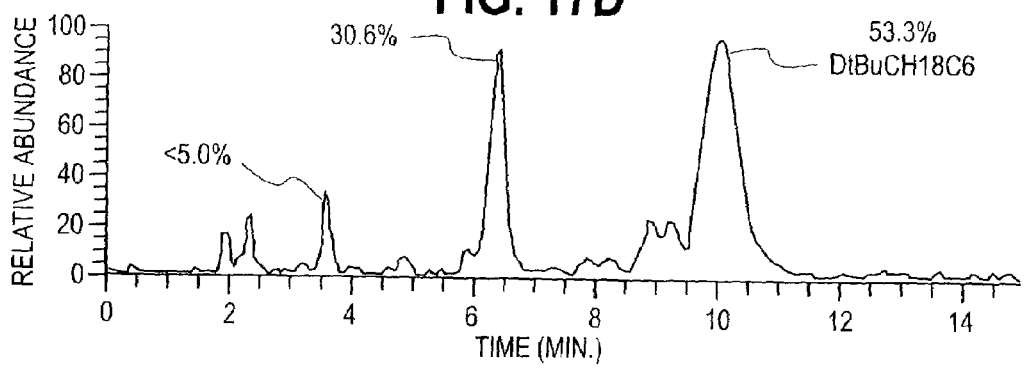

PURIFICATION OF 4,4'(5')-DI-T-BUTYLCYCLOHEXANO-18-CROWN-6

CROSS-REFERENCE TO RELATED APPLICATION

This is a continuation-in-part of provisional application Ser. No. 60/335,991 filed on Nov. 15, 2001.

BACKGROUND ART

The synthesis of extractant hosts such as the macrocyclic crown ethers (including their nitrogen and sulfur substituted analogs), porphyrins, cryptands, calixarenes, and the like, frequently afford mixtures of the desired (predetermined) macrocyclic extractant molecule and acyclic starting materials and/or partial reaction products. In addition to the presence of these synthesis reaction byproducts, different stereochemical conformations of the predetermined macrocyclic extractant can also be present (e.g., the cone, partial cone, 1,2-alternate, and 1,3-alternate conformations of calix [4]arene), and purification is frequently required to isolate the most desirable stereoisomer(s) for a given application.

The crown ether 4,4'(5')-di-t-butylcyclohexano-18-crown-6 (DtBuCH18C6, FIG. 1) is illustrative of a highly selective extractant for the removal of $Sr^{2+}$ and $Pb^{2+}$ from acidic solutions that has been used over the past ten years in solvent extraction-based separations for the removal of the highly radioactive $^{90}Sr$ fission product from acidic nuclear wastes [Horwitz et al., *Solvent Extr. Ion Exch.* (1990), 8, 557–572; Horwitz et al., *Solvent Extr. Ion Exch.* (1991), 9, 1–25; Horwitz et al., U.S. Pat. No. 5,100,585 (1992); Horwitz et al., U.S. Pat. No. 5,344,623 (1994); Law et al., INEEL/EXT-97-00832; Idaho National Engineering Laboratory; Idaho Falls, Id., 1997; Wood et al., INEEL/CON—97-01431; Idaho National Environmental and Engineering Laboratory; Idaho Falls, Id., 1998; and Horwitz et al., In *Metal-Ion Separation and Preconcentration: Progress and Opportunities*; Bond et al. Eds.; American Chemical Society: Washington, D.C., 1999; Vol. 716, pages 20–50] and in extraction chromatographic resin-based separations for $Sr^{2+}$ [Horwitz et al., *Anal. Chem.* (1991), 63:522–525; Horwitz et al., *Solvent Extr. Ion Exch.* (1992), 10:313–336; Horwitz et al., U.S. Pat. No. 5,110,474, (1992); Horwitz et al., U.S. Pat. No. 5,346,618, (1994); and Dietz et al., In *Metal-Ion Separation and Preconcentration: Progress and Opportunities*; Bond et al. Eds.; American Chemical Society: Washington, D.C., (1999); Vol. 716:234–250] and $Pb^{2+}$ [Horwitz et al., *Solvent Extr. Ion Exch.* (1992), 10:313–336] analyses of terrestrial, aquatic, and bioassay samples.

The DtBuCH18C6 molecule can theoretically have 128 different isomeric designations; however, 20 diastereomers for each of the two t-butyl-substituted regioisomers (i.e., 4,4' and 4,5') result in only 40 symmetrically nondegenerate isomers. Due to differences in the conformation of the t-butylcyclohexano substituents (i.e., cis-syn-cis, cis-anti-cis, etc.), each of the different stereoisomers of DtBuCH18C6 can exhibit different cation complexation strengths. [Izatt et al., *Chem. Rev.* (1991) 91:1721–2085; Hay et al., RL3-6-C3-31; Pacific Northwest National Laboratory; Richland, Wash., (1996) and Hay, In *Metal-Ion Separation and Preconcentration: Progress and Opportunities*; Bond, et al. Eds.; American Chemical Society: Washington, D.C., (1999) Vol. 716:102–113.] Specifically, the cis/trans and cross-ring syn/anti conformational differences can effect diminished cation extraction arising from steric constraints imposed by the t-butylcyclohexano substituents, severely distorted oxygen donor arrays, and/or poor preorganization for cation complexation that requires a conformational rearrangement at a thermodynamic expense.

As a result of the application of DtBuCH18C6 in the removal of $^{90}Sr$ from acidic nuclear wastes, as noted before, molecular modeling calculations have been performed to determine which of the 40 different isomers is the most efficient for the extraction of $Sr^{2+}$ from $HNO_3$. [Hay et al., RL3-6-C3-31; Pacific Northwest National Laboratory; Richland, Wash., (1996) and Hay, In *Metal-Ion Separation and Preconcentration: Progress and Opportunities*; Bond, et al. Eds.; American Chemical Society: Washington, D.C., (1999) Vol. 716:102–113.] Of the two isomers depicted in FIG. 1, molecular mechanics calculations have predicted that 4(z),4'(z)-cis-syn-cis-DtBuCH18C6 forms the most thermodynamically stable complexes with $Sr^{2+}$, whereas 4(z),5' (e)-cis-anti-cis-DtBuCH18C6 is predicted to form the least stable complexes.

The effects of conformational preorganization, which derive primarily from stereoisomerism rather than regioisomerism in this class of compounds, on the predicted distribution ratios for $Sr^{2+}$ ($D_{Sr}$) are remarkable: $D_{Sr} \approx 10$ for 4(z),4'(z)-cis-syn-cis-DtBuCH18C6 and $D_{Sr} \approx 0.022$ for 4(z),5'(e)-cis-anti-cis-DtBuCH18C6 (0.1 M solutions in 1-octanol and 1 M $HNO_3$). [Hay et al., RL3-6-C3-31; Pacific Northwest National Laboratory; Richland, Wash., (1996) and Hay, In *Metal-Ion Separation and Preconcentration: Progress and Opportunities*; Bond, et al. Eds.; American Chemical Society: Washington, D.C., (1999) Vol. 716:102–113.] These calculations clearly illustrate the significant impact that stereoisomeric effects can have on the efficiency of a given separation using dicyclohexano-18-crown-6 (DCH18C6)-based extractants and also point to the need for purification methods permitting the isolation or enrichment of those isomers having the most efficient $Sr^{2+}$ extraction properties.

The catalytic hydrogenation of the di-t-butylbenzo-18-crown-6 (DtBuB18C6, FIG. 2) precursor of DtBuCH18C6 results in the formation of synthesis byproducts, the most frequently encountered of which are shown in FIG. 2. The catalytic hydrogenation of DtBuB18C6 can be presumed to occur in a step-wise manner to yield first 4-t-butylbenzo-4' (5')-t-butylcyclohexano-18-crown-6 [(tBuB)(tBuCH)18C6] and finally DtBuCH18C6, which are depicted in the left column of FIG. 2. Depending on the hydrogenation conditions [Gula et al., U.S. Pat. No. 5,478,953 (1995)] and the activity of the heterogeneous rhodium (Rh) catalyst, ring cleavage reactions can produce a variety of acyclic molecules, and several possibilities are depicted in the right column of FIG. 2.

Continuing work on the purification of extractant molecules such as DtBuCH18C6 and the isolation of those stereoisomers predicted to be the most efficient $Sr^{2+}$ extractants (i.e., 4(z),4'(z)-cis-syn-cis-DtBuCH18C6) has provided several strategies for the purification of predetermined extractants such as the stereoisomers of DtBuCH18C6 from the various aryl-containing under-hydrogenation products, ring cleavage products, and other inactive stereoisomers. The disclosure that follows describes two precipitation-based methods and a versatile method that utilizes solvent extraction third phase formation that can be used to purify impure samples and also to enrich the sample in the desired isomers; the latter method meeting several success criteria important to commercial application.

BRIEF SUMMARY OF THE INVENTION

The present invention contemplates purification of a predetermined water-insoluble extractant that can be present along with one or more other extractants, starting materials, or reaction products. Thus, one aspect of the invention contemplates a method for purifying a predetermined water-insoluble extractant from a composition containing one or more additional extractants, synthesis reaction starting materials and reaction byproducts; i.e., the composition can contain one or more of each of additional extractants, synthesis reaction starting materials and reaction byproducts. In accordance with that method, a liquid phase composition is provided that contains the predetermined extractant and one or more additional extractants, synthesis reaction starting materials and reaction byproducts that are dissolved as solutes in an organic diluent. An ion-containing compound such as a metal salt is admixed with the composition to form a predetermined extractant/ion complex in the organic diluent phase that has an affinity for a new phase that is greater than the affinity for the first-named phase. The predetermined extractant/ion complex is separated from the diluent by using the new phase affinity, and the predetermined extractant/ion complex is preferably although not necessarily recovered. The predetermined extractant/ion complex is separated into extractant and ion. The predetermined extractant is recovered.

Exemplary predetermined extractants include a macrocyclic or acyclic polyether, polyamine, polythioether, a calixarene, a cryptand and a porphyrin. Illustrative organic diluents include a $C_1$–$C_5$ alcohol, a $C_3$–$C_9$ ketone, a $C_2$–$C_6$ ether, a poly($C_2$–$C_6$)ether, a $C_5$–$C_{14}$ straight chain alkane, a $C_5$–$C_{14}$ branched chain alkane, a $C_6$–$C_{12}$ aromatic solvent, and a mixture of one or more such diluents. Exemplary ion-containing compounds include a cation such as an ammonium ion, a potassium (I) ion, a rubidium (I) ion, a cesium (I) ion, a silver (I) ion, a thallium (I) ion, a calcium (II) ion, a strontium (II) ion, a barium (II) ion, a cadmium (II) ion, a lead (II) ion, a mercury (II) ion, a scandium (III) ion, an yttrium (III) ion, a lanthanum (III) ion, a lanthanide (III) ion (i.e., Ce—Lu) and a bismuth (III) ion. Exemplary anions of an ion-containing compound include an anion selected from the group consisting of nitrate, nitrite, perchlorate, perbromate, periodate, chloride, bromide, iodide (halide).

In some aspects, the extractant/ion complex has a greater affinity for a new phase that is a solid phase, whereas in other aspects the extractant/ion complex has a greater affinity for another liquid phase than for the diluent-containing phase. Preferably, the extractant/ion complex exhibits a greater affinity for a solvent extractant third phase that is formed by admixture of an aqueous solution of the compound with a water-immiscible organic diluent phase.

The present invention has several benefits and advantages.

One benefit of the invention is that third phase formation is a robust purification strategy for purification of DtBuCH18C6 that is effective for different batches of DtBuCH18C6 that contain different impurities at varying concentrations.

An advantage of extractant purification by third phase formation is the balance between purity and yield obtained through its use, while affording a product with $D_{Sr}$ greater than 3.5 in less than four hours of effort in the laboratory.

Another advantage of the invention is that a contemplated method uses inexpensive common laboratory chemicals, does not require special laboratory apparatus, and can be performed by a well-trained technician.

Another benefit of the invention is that several variables related to purification via third phase formation (i.e., organic diluent, aqueous phase acidity, and extracted solute) can be readily adjusted to provide extractants of a desired purity in good yield.

Still further benefits and advantages will be apparent to the skilled worker from the disclosure that follows.

BRIEF DESCRIPTION OF THE DRAWINGS

In the drawings forming a portion of this disclosure,

FIG. 2 shows structural formulas of six molecules most frequently encountered in the catalytic hydrogenation of DtBuB18C6 to produce DtBuCH18C6. Appropriate chemical names, abbreviated names used herein and retention times (RT) in the reverse phase liquid chromatography-mass spectral (RPLC-MS) protocol are also reported for each molecule;

FIG. 15 in four panels shows RPLC-MS chromatograms of Batch 585 of DtBuCH18C6 extractant untreated (D$_{Sr}$=3.0.

FIG. 16 in four panels is substantially like FIG. 15, except that Batch 585 of DtBuCH18C6 extractant was used and n-heptane was used as diluent, and wherein

FIG. 17 in four panels is substantially like FIG. 16, except that Batch 590–2 of DtBuCH18C6 extractant was used, and wherein FIG. 17A shows the untreated material, FIG. 17B shows purification from 3.0 M HCl (33.5% recovery), FIG. 17C shows purification from 4.5 M HCl (54.1% recovery), and FIG. 17D shows purification from 6.0 M HCl (>100% recovery);

DETAILED DESCRIPTION OF THE INVENTION

The present invention contemplates purification of a predetermined water-insoluble extractant that can be present along with one or more other extractants, starting materials and reaction products. Typical predetermined extractants contemplated here are used to extract a predetermined ion from an aqueous composition as in the extraction of a radioactive isotope from an acidic solution.

One aspect of the invention contemplates a method for purifying a predetermined water-insoluble extractant from a composition containing one or more additional extractants, synthesis reaction starting materials and reaction byproducts. In accordance with this method, a liquid phase composition is provided that contains the predetermined extractant and one or more additional extractants, synthesis reaction starting materials and reaction byproducts dissolved as solutes in an organic diluent. An ion-containing compound is admixed with the composition to form an extractant/ion complex in the organic diluent phase that has an affinity for a new phase that is greater than the affinity for the first-named phase. If the ion also forms a further complex with the one or more additional extractants, synthesis reaction starting materials and reaction byproducts that may be present in the composition, any such further complex formed exhibits less of an affinity for the second phase than does the predetermined extractant/ion complex. The predetermined extractant/ion complex is separated from the diluent by using the new phase affinity. The predetermined extractant/ion complex is separated into extractant and ion-containing compound, with or without a separate step of recovering the predetermined extractant/ion complex. The predetermined extractant is recovered.

Exemplary predetermined extractants include a macrocyclic (FIGS. 1 and 2) or acyclic polyether (FIG. 2), a cyclic polyamine (shown hereinafter), a cyclic polythioether (shown hereinafter), a calixarene (shown hereinafter), a cryptand (shown hereinafter) and a porphyrin.

Figure 1A:
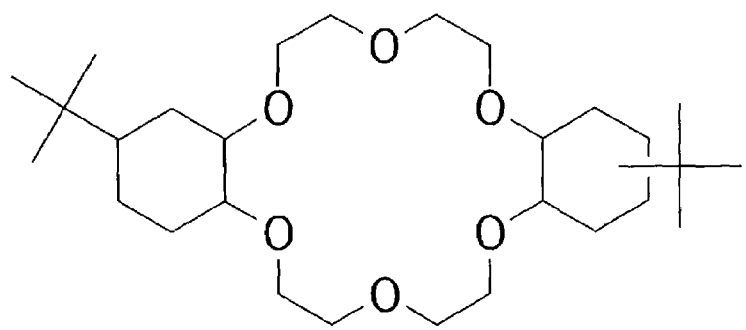
FIG. 1 is a generic representation of di-t-butylcyclohexano-18-crown-6 (FIG. 1A) and two of its 40 different isomers (FIGS. 1B and 1C)
Figure 1B:
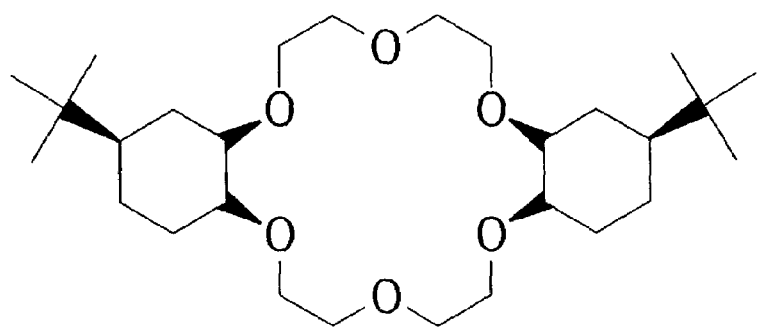
Figure 1C:
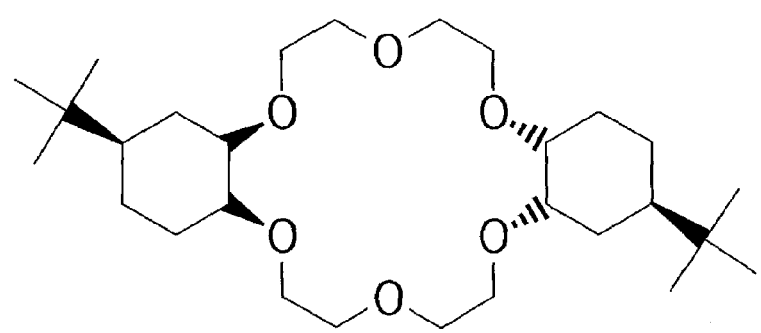

Exemplary macrocyclic polyethers include the crown ethers such as those known as 15-crown-5, 18-crown-6, 21-crown-7 and the like. Bis-ring-substituted macrocyclic polyethers such as dibenzo-18-crown-6 and dicyclohexano-18-crown-6, are preferred. D$_1$–C$_1$–C$_6$-alkyl-substituted-bis-ring-substituted macrocyclic ethers are still more preferred. 4,4'(5')-di-t-butylcyclohexano-18-crown-6 (DtBuCH18C6), which can exist in several stereoisomeric forms of which two are shown in FIG. 1, is a particularly preferred extractant and is used herein as illustrative. The compounds on the left-hand side of FIG. 2 illustrate other ring-substituted macrocyclic ether extractants, particularly those that can be present as impurities in a composition containing DtBuCH18C6 as the predetermined extractant to be purified. Oligo- and poly(ethylene oxides) and poly(propylene oxides) exemplify unsubstituted and C$_1$–C$_6$-hydrocarbyl-substituted acyclic polyether extractants, whereas the several compounds shown on the right-hand side of FIG. 2 exemplify ring-substituted acyclic polyethers.

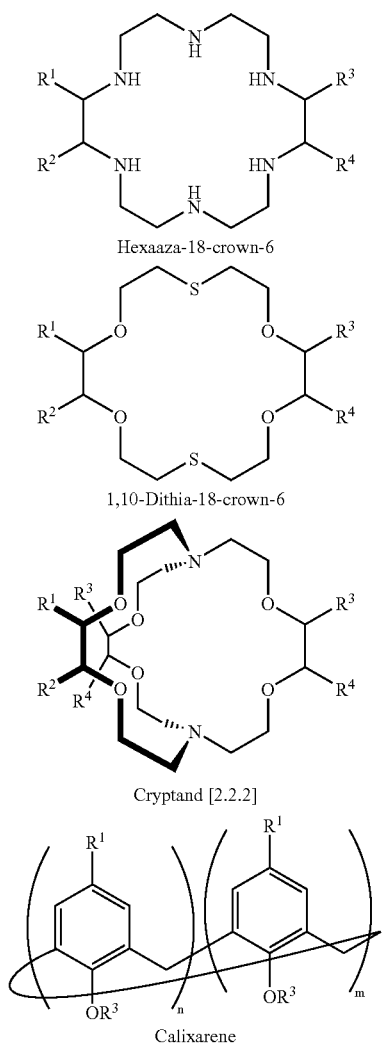

The $R^1$, $R^2$, $R^3$, $R^4$, $R^5$ and $R^6$ substituent groups for all but the calixarene can be the same or different and are selected from the group consisting of a hydrido (H), a $C_1$–$C_{10}$ normal or branched hydrocarbyl group, a $C_5$–$C_8$cyclohydrocarbyl group, a $C_1$–$C_6$ normal or branched hydrocarbyl-substituted cyclohydrocarbyl group (e.g., t-butylcyclohexano), an aromatic group, and $C_1$–$C_6$ normal or branched hydrocarbyl-substituted aromatic group such as t-butylbenzo.

For the calixarene, $R^1$, $R^2$, $R^3$ and $R^4$ substituent groups can be the same or different and can be selected from the group consisting of a hydrido (H), $C_1$–$C_{10}$ normal or branched hydrocarbyl, ether, polyether, polyamine, polythioether, hydroxyl, carboxyl, sulfonyl, or phosphonyl group. $R^3$ and $R^4$ substituent groups are most commonly and preferably hydrido or methyl. The sum of subscripts n and m (m +n) can be 4 through 8. Most commonly n+m=4, 6, or 8. Of the possible combinations, n+m+n+m (i.e., alternating) are the most important, although n+n+m+m (i.e., blocks such as n=2 and m=2) can be prepared. Odd numbered rings with n+m=5 or 7 are less frequently encountered. The odd numbered rings typically are "synthesis reaction byproducts" from which a calix[4]arene (i.e., n+m+n+m=4) or calix[6]arene is purified by third phase formation.

The word "hydrocarbyl" is used herein as a convenient term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; that is, $C_1$–$C_4$ alkyl, methyl, or dodecenyl. Exemplary hydrocarbyl groups contain a chain of 1 to about 12 carbon atoms, and preferably one to about 10 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, iso-butyl, sec-butyl, tert-butyl, pentyl, iso-amyl, hexyl, n-heptyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like. Corresponding ether or alkoxy groups contain an above alkyl group bonded to an oxygen atom that is also bonded to the cation ring.

Illustrative organic diluents include a $C_1$–$C_5$ alcohol, a $C_3$–$C_9$ ketone, a $C_2$–$C_6$ ether, a poly($C_2$–$C_6$)ether, a $C_5$–$C_{14}$ straight chain, branched chain or cyclic alkane, and a $C_6$–$C_{12}$ aromatic solvent. These solvents are well-known to workers of ordinary skill and can be selected from well-known handbooks, catalogues and the like. Exemplary particularly preferred organic diluents include iso-propyl alcohol, methyl isobutyl ketone (MIBK), methyl t-butyl ether (MTBE), ethylene glycol dimethyl ether (glyme), n-heptane, and toluene. Particularly preferred diluents are $C_6$–$C_{12}$ straight chain, branched chain and cyclic alkanes and $C_6$–$C_9$ aromatic solvents such as hexane, heptane, octane, nonane, decane, dodecane, iso-octane, 2-methylhexane, 3-methylhexane, 2,3-dimethylpentane, 2,4-dimethylpentane, 2,2,3-trimethylpentane, 2,2,4-trimethylpentanne, 2,2,5-trimethylhexane, cyclohexane, cycloheptane, methylcyclohexane, ethylcyclohexane, and benzene, toluene, ethylbenzene, isopropylbenzene, mesitylene, and a xylene, respectively. In many instances where water is used in a purification, it is preferred that the organic diluent be non-miscible with water, and more preferably, dissolve less than about 2 percent by volume of water.

An ion-containing compound contains a cation and an anion. Anionic and uncharged extractants usually form complexes with cations, whereas cationic extractants usually form complexes with anions, although some amine-containing extractants can also extract cations at appropriate pH values.

Contemplated exemplary cations present in an ion-containing compound include monovalent, divalent and trivalent cations. Illustrative cations include an ammonium ion, a potassium (I) ion, a rubidium (I) ion, a cesium (I) ion, a silver (I) ion, a thallium (I) ion, a calcium (II) ion, a strontium (II) ion, a barium (II) ion, a cadmium (II) ion, a lead (II) ion, a mercury (II) ion, a scandium (III) ion, an yttrium (III) ion, a lanthanum (III) ion, a lanthanide (III) (i.e., Ce—Lu) ion and a bismuth (III) ion. A hydronium ion can also be useful in a purification by third phase formation. A mixture of two or more of the above cations can also be used.

Contemplated anions are preferably monovalent and are a counterion of a strong acid. Exemplary anions of an ion-containing compound include an anion selected from the group consisting of nitrate, nitrite, perchlorate, perbromate, periodate, chloride, bromide, iodide (halide), with chloride being particularly preferred.

Hard Lewis acid cations are preferably used to form complexes with extractants containing oxygen donors such as the illustrative DtBuCH18C6, whereas soft Lewis acids are typically utilized to form complexes with polythioether or polyamine extractants. Soft Lewis acid cations are also typically utilized to form complexes with polyamine, cryptand and porphyrin extractants, as are hydrogen bond donors (when in basic media) and hydrogen bond acceptors (when in acid media). Calixarene extractants can have oxygen, nitrogen, and/or sulfur donor atoms and the cation used for complex formation is chosen accordingly. Strontium chloride is a particularly preferred compound for use in purifying the ring-substituted macrocyclic ethers used as illustrative herein.

The ion-containing compound can be admixed with the organic diluent-containing extractant in solid form (in the absence of a solvent such as water) as by admixture of solid compound particles with the organic diluent phase, or the ion-containing compound can be dissolved in a solvent such as water when the admixture occurs to form the extractant/ion complex. Illustrative admixture can occur by shaking, stirring or grinding the two ingredients together, as may be appropriate to the form of the phase in which the ion-containing compound is initially present.

The extractant/ion complex that is formed has an affinity for a new phase that is greater than the affinity for the first-named phase. In some aspects, that new phase is a solid phase, whereas in other aspects the extractant/ion complex has a greater affinity for another liquid phase than for the diluent-containing phase. Preferably, the extractant/ion complex exhibits a greater affinity for a solvent extractant third phase as is discussed hereinafter.

In some aspects, the extractant/ion complex precipitates directly and therefore has a greater affinity for a new solid phase than for the first-named, organic diluent-containing phase. In other aspects, the new solid phase comprises an exchange resin to which the formed complex preferentially binds. In still other aspects, the complex is indirectly precipitated from the diluent phase by the addition of a further diluent that is miscible with the first-named organic diluent to form a new mixed organic diluent from which the extractant/ion complex precipitates as a new solid phase.

In still more preferred practice, the ion-containing compound is dissolved in water, the organic diluent phase containing one or more of the predetermined extractant, synthesis reaction byproducts, and starting materials is not miscible with water, and the admixture of the immiscible aqueous and light organic phases that contains the extractant/ion complex causes a new third phase to form. That new third phase contains the extractant/ion complex; that is, the extractant/ion complex exhibits a greater affinity for that new third phase than for either of the other two phases. Preferably, that third phase is more dense than water and forms beneath the water layer, providing an easy means for separation of the predetermined extractant/ion complex from the light organic (which contains the impurities) and water phases. The phrase "third phase" is used interchangeably herein with the phrase "heavy organic phase". The third phase can have a density that is less than that of water or that of the organic diluent, but it is preferred that the third phase have a density that is greater than either that of the extracted, "light organic phase" or the aqueous phase.

The predetermined extractant/ion complex is thereafter separated into the predetermined extractant, which has been purified by the preceding steps, and an ion-containing compound. Where a predetermined extractant/ion complex precipitates or is precipitated, that solid complex can be recovered prior to separating the predetermined extractant from the complexed ion. Such recovery is not necessary as where a third phase is formed that contains the desired complex as well as liquid components such as the organic diluent. It is contemplated, however, that the phase containing the predetermined extractant/ion complex be segregated from the other phases so that the purified predetermined extractant can ultimately be obtained.

The new third phase or collected precipitate can be suspended in a suitable water-immiscible organic diluent and extracted one or more times with water or dilute acid as desired to remove the complexed ion along with its counterion. If desired, and depending upon the ions utilized, a water-soluble compound, one of whose ions forms a precipitate with the complexed ion, can be admixed with the organic diluent composition to remove the ion from the complex, to provide the purified predetermined extractant that can be recovered by removal of the organic diluent.

It should be understood that a contemplated purification can utilize a plurality of the above-described purification techniques, or the same technique more than once to obtain a desired level of purity. Thus, for example, a predetermined extractant/ion complex can be precipitated twice or more from the same or different organic diluent, or a single precipitation can be followed by purification by third phase formation, or vice versa.

When third phase formation is utilized for carrying out the desired purification, it is preferred that the extractant be present in the organic diluent at a concentration of about 0.25 molar (M) up to the limit of solubility or viscosity that can be conveniently manipulated. Typically, the upper limit of concentration is about 1 to about 2 M, with toluene and n-heptane being particularly preferred organic diluents.

The compound concentration used can depend upon the solubility of the compound and the constitution of the aqueous composition. The compound concentration in the aqueous phase used for third phase formation is typically about 0.05 to about 4 M, and preferably about 0.5 to about 1.5 M. In addition, if a strongly acidic aqueous solution is used, the compound concentration can tend toward the lower side of the above range. More preferably, a compound concentration of about 0.5 to about 1.5 M in aqueous acid solution is used.

More preferably still, the ion-containing compound concentration used is a substoichiometric amount based on an assay of the extractant to be purified. Thus, a composition containing a predetermined extractant with contaminating amounts of a starting material, a reaction product, or another extractant is assayed to determine the amount of predetermined extractant present. Based upon that assay, a substoichiometric amount of ion-containing compound is admixed with the composition to form the desired complex. It has been found that admixture of the compound in an amount of about 90 mole percent of the amount of predetermined extractant provides a good balance between yield and purity of the resultant predetermined extractant.

Exemplary strong acids for this use include the previously mentioned strong acids such as nitric acid, hydrochloric acid and perchloric acid present at about 0.5 M to concentrated acid. The acid is preferably present at about 3 to about 5 M for ring-substituted macrocyclic ether extractants such as DtBuCH18C6, and up to about 6 M for acyclic polyether, polythioether, calixarene, cryptand and similar extractants.

Any of the purifications discussed herein can be carried out at a temperature of about 100 to about 70° C. More preferably, a contemplated purification is carried out at an ambient temperature of about 200 to about 300 C.

Figure 3A:
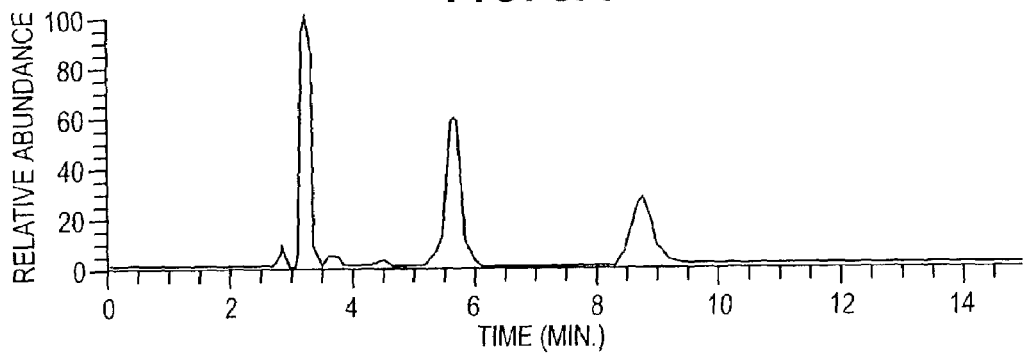
FIG. 3 in four panels shows a plot of chromatographic results for untreated DtBuCH18C6 Batch 492 extractant (FIG. 3A), and chromatographic results from three samples taken from a preparative-scale TLC (PTLC) study whose $R_f$ values in that separation were 0.65, 0.54 and 0.42 for the materials of FIGS. 3B, 3C and 3D, respectively.
Figure 3B:
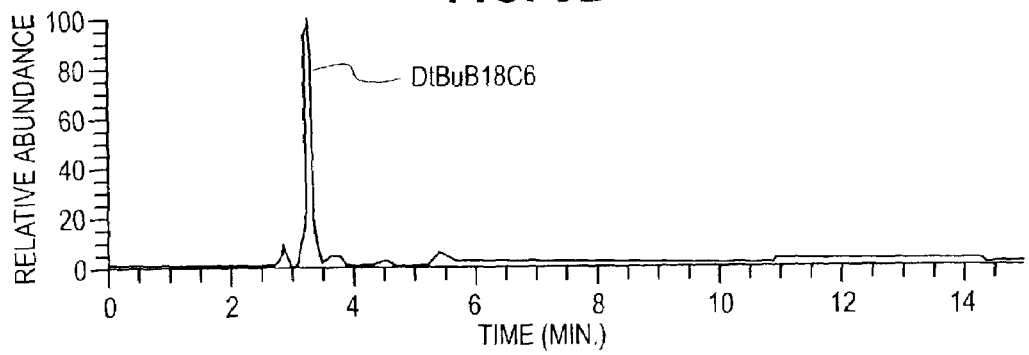
Figure 3C:
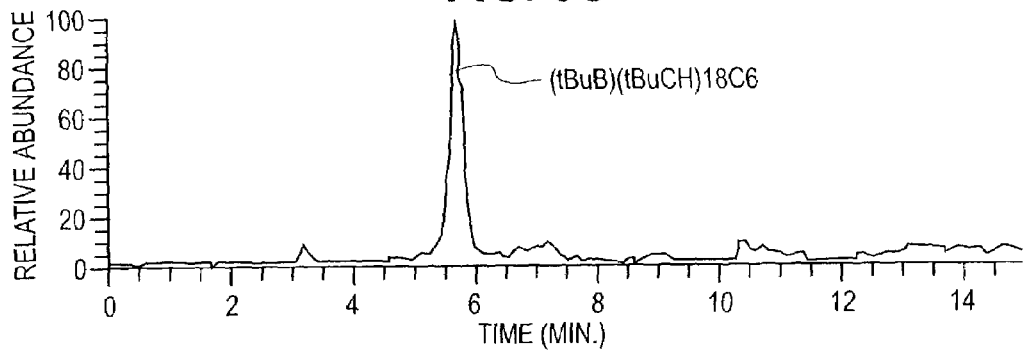

As mentioned previously, a variety of reaction byproducts (FIG. 2) can be formed during the hydrogenation of DtBuB18C6 depending upon the synthesis conditions and catalyst activity. In order to accurately identify and quantify these reaction byproducts in untreated and purified samples of DtBuCH18C6, an analytical method using RPLC-MS was developed and qualified. FIG. 3A shows the RPLC-MS chromatogram of a partially hydrogenated DtBuCH18C6 Batch 492 as well as chromatograms (FIGS. 3B–D) for each of three bands separated by preparative-scale thin layer chromatography (PTLC). The PTLC study was performed to confirm the band assignments in the TLC screening method and also as a probe of the potential effectiveness of normal phase preparative-scale high performance liquid chromatography (HPLC) for the purification of DtBuCH18C6.

Figure 3D:
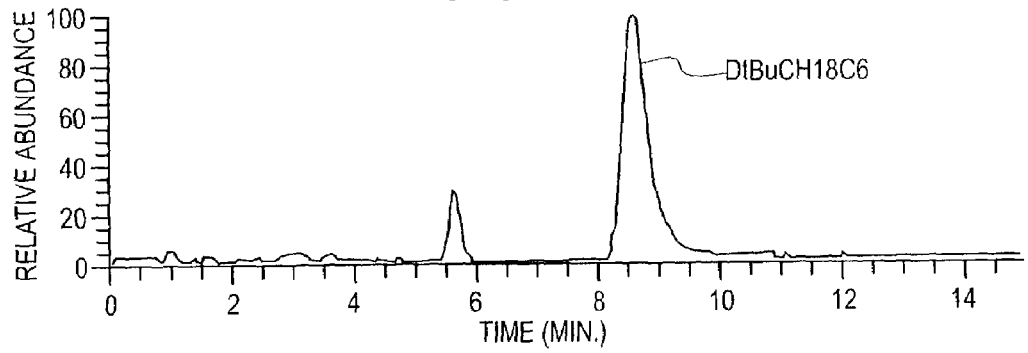
Figure 4A:
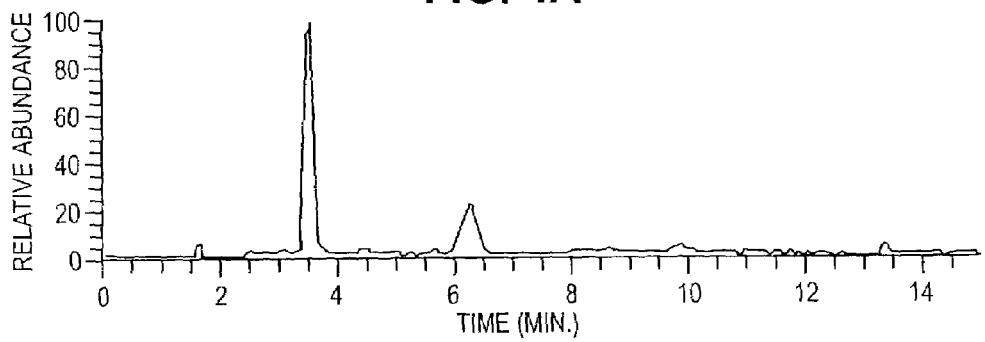
FIG. 4 in four panels shows a plot of RPLC-MS results for progress of a typical catalytic hydrogenation of DtBuB18C6 Batch 589 extractant over time after 1, 2, 18 and 42 hours in FIGS. 4A, 4B, 4C and 4D, respectively, to produce (tBuB)(tBuCH)18C6 and, ultimately, DtBuCH18C6.
Figure 4B:
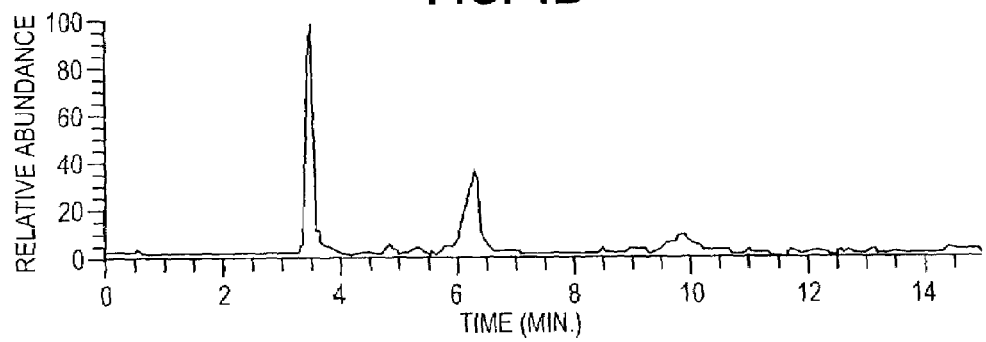
Figure 4C:
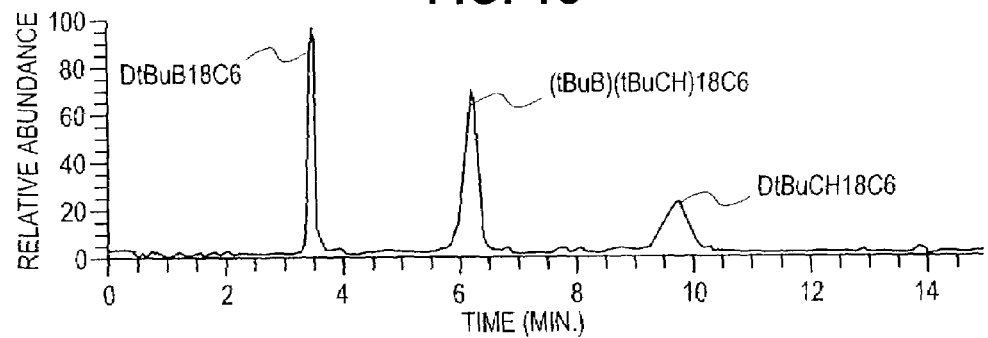
Figure 4D:
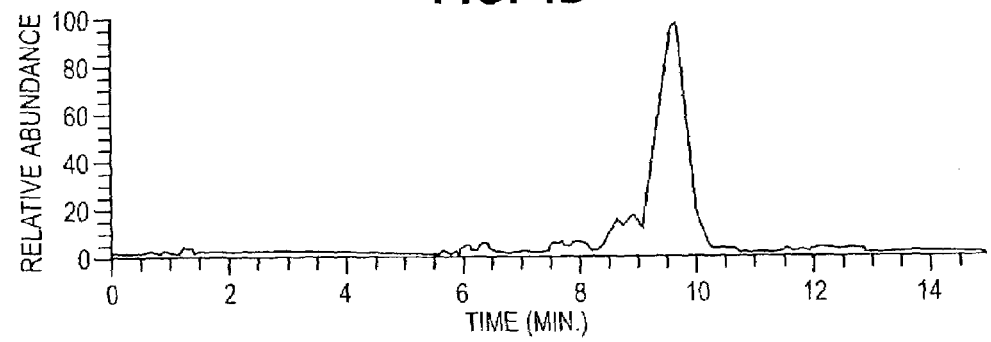

FIG. 3D shows that DtBuB18C6 and (tBuB)(tBuCH) 18C6 can be effectively separated from DtBuCH18C6 using 10 percent $CH_3OH$ in $CH_2Cl_2$ on silica gel PTLC plates ($R_f$=0.42: (tBuB) (tBuCH)18C6=10.8 percent and DtBuCH18C6=85.4 percent). FIG. 3 also provides valuable information relating to the retention times of reasonably pure samples of DtBuB18C6, (tBuB)(tBuCH)18C6, and DtBuCH18C6 in the RPLC-MS method. A close examination of the chromatograms shows that the band for DtBuB18C6 is narrow because only two t-butyl-substituted regioisomers exist, but the bands become progressively wider when regioisomers and stereoisomers coexist [e.g., (tBuB)(tBuCH)18C6 and DtBuCH18C6].

FIG. 4 is a chromatogram that shows the progress of a typical hydrogenation reaction of DtBuB18C6. After one hour of hydrogenation (FIG. 4A), the mixture contains 30.2 percent (tBuB)(tBuCH)18C6; at two hours (FIG. 4B) (tBuB) (tBuCH)18C6 reaches 38.1 percent and 12.2 percent DtBuCH18C6 appears. It is only after 18 hours of reaction (FIG. 4C) that substantial hydrogenation is observed with (tBuB)(tBuCH)18C6 and DtBuCH18C6 reaching 44.5 and 25.5 percent, respectively. After 42 hours of reaction, no DtBuB18C6 or (tBuB)(tBuCH)18C6 are detectable by RPLC-MS.

Figure 5A:
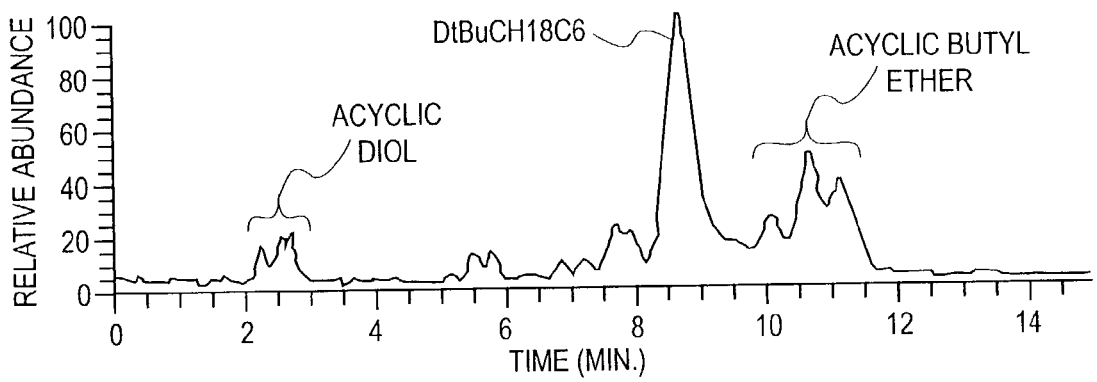
FIG. 5 in three panels shows RPLC-MS chromatograms of three batches of DtBuCH18C6 extractant (#527 in FIG. 5A; #574 in FIG. 5B and #585 in FIG. 5C) showing the approximate elution times of the extractant and impurities encountered in this work.
Figure 5B:
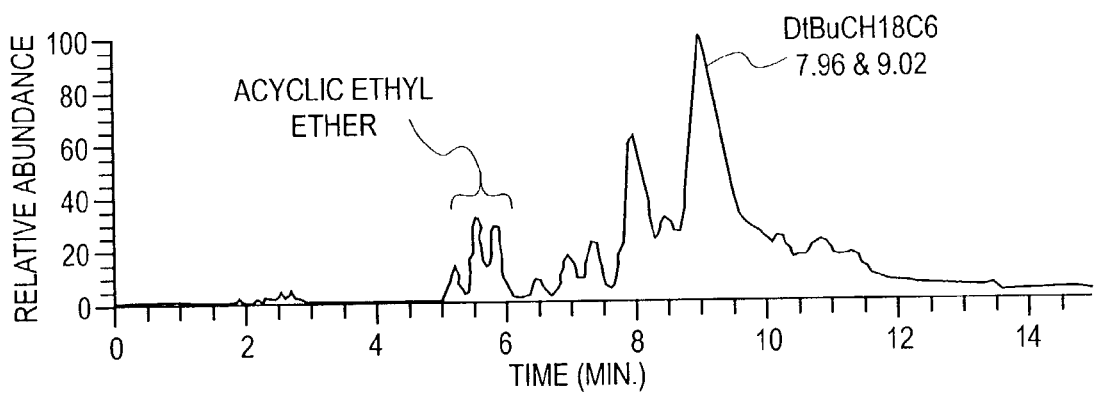
Figure 5C:
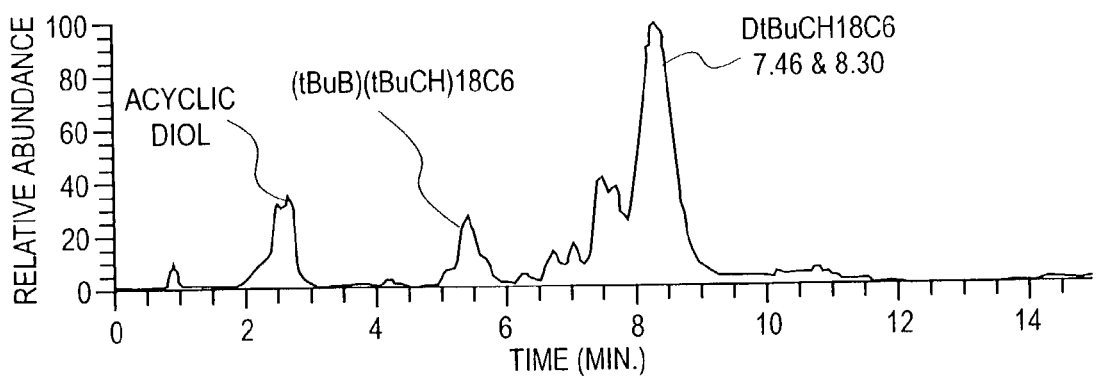

Although the results of FIG. 4 show the products present in a typical hydrogenation run, FIG. 5 shows examples of several hydrogenation reactions in which the catalyst activity and reaction conditions varied to produce complex mixtures of the molecules shown in FIG. 2. Such combinations of ring-substituted acyclic diols, ring-substituted acyclic ethers, aryl-containing macrocycles, and isomers of DtBuCH18C6 place severe demands on the contemplated purification processes, especially if a single method is to be universally successful in the separation of DtBuCH18C6 from such complicated mixtures.

Commercial Aspects

Several success criteria were established to guide the development of an effective, convenient, and economically viable purification method for DtBuCH18C6 in a commercial context:

(1) Purified product should have a strontium distribution ratio ($D_{Sr}$ value) greater than 3.5 from 1.0 M $HNO_3$;

(2) Yield of greater than 65 percent of greater than 80 percent pure DtBuCH18C6;

(3) Ease of use at greater than 100 g scale (i.e., no special chemicals or equipment);

(4) Processing time less than 8 hours.

Use of the above criteria eliminated a variety of potential purification methods including preparative-scale HPLC based on the successful PTLC separations shown in FIG. 3. Furthermore, multiple attempts using low pressure chromatography [Dietz et al., Sep. Sci. Technol. (1999) 34:2943–2956] and preparative-scale HPLC [results not shown] afforded in impractically low yields of DtBuCH18C6, even at low column loadings (i.e., less than 20 g). Given the complicated multicomponent mixture and the constraints imposed by these success criteria, three potential schemes for the purification of DtBuCH18C6 emerged:

(1) Direct precipitation of predetermined extractant/ion complex;

(2) Induced precipitation of predetermined extractant/ion complex; and (3) Solvent extraction third phase formation.

Each of these purification methods involves cation coordination by the extractant, here, illustratively a crown ether, prior to precipitation or exclusion of the less soluble ion pair complex from an organic medium (i.e., having a greater affinity for another phase).

Altering macrocycle phase affinity by complex formation has long been used and is the principle behind the separation of the cis-syn-cis and cis-anti-cis stereoisomers of DCH18C6. [Izatt et al., Inorg. Chem. (1975) 14:3132–3133.] This method uses perchloric acid ($HClO_4$) to precipitate [($H_3O$) (cis-syn-cis-DCH18C6)] [$ClO_4$] [Simonov et al., Dokl. Akad. Nauk SSSR (1983) 272:1129] from a mixture of the cis-syn-cis- and cis-anti-cis-DCH18C6 isomers, followed by the addition of excess $PbCO_3$ to consume acid and precipitate [$Pb(OH_2)_2$(cis-anti-cis-DCH18C6)] [$ClO_4$]$_2$. [Rogers et al., J. Chem. Crystallogr. (1997) 27:263–267.] Such solubility differences have led to modified $HClO_4$-based precipitation strategies for the purification of DtBuCH18C6 [Dietz et al., Sep. Sci. Technol. (1999) 34:2943–2956], but these approaches are not amenable for scale-up to multigram quantities due to the hazards associated with perchlorate compounds, low yields, and lengthy processing times.

In order to limit as much as possible the complexation of the solubility-altering cation to the predetermined DtBuCH18C6 extractant, substoichiometric quantities of $Sr^{2+}$ were employed because this cation is known to form highly stable complexes with 18-membered macrocycles [Izatt et al., Chem. Rev. (1991) 91:1721–2085] and it is readily extracted from $HNO_3$-and HCl-containing aqueous media by DCH18C6 and DtBuCH18C6 [as noted before and in Horwitz et al., Solvent Extr. Ion Exch. (1990) 8:199–208; Dietz et al., Radiochim. Acta (1999) 85:119–129; Bond et al., Anal. Chem. (1999) 71:2757–2765; Dietz et al., J. Chem. Soc., Chem. Commun. (1999) 1177–1178; Chiarizia et al., Solvent Extr. Ion Exch. (2000), 18:451–478; and Bond et al., Ind. Eng. Chem. Res. (2000) 39:3432–3464]. Maximizing the extent of interaction between $Sr^{2+}$ and DtBuCH18C6 also serves to minimize the presence of synthesis reaction byproducts in the purified material because such molecules are weaker ligands than DtBuCH18C6 and they remain soluble in the organic medium, whereas the [Sr(DtBuCH18C6)]$^{2+}$ complex has a greater affinity for another solid or liquid phase. Thus, a substoichiometric quantity of $Sr^{2+}$, relative to the possible DtBuCH18C6 content of the as-hydrogenated material, was used as a means of introducing selectivity for DtBuCH18C6 into the purification process.

Initial studies were focused on the precipitation of $Sr^{2+}$ complexes of DtBuCH18C6 involving relatively nontoxic and nonhazardous anions, and the precipitation of [Sr(DtBuCH18C6)]$^{2+}$ complexes with the common inorganic anions $NO_3^-$ or $Cl^-$ seemed a logical starting place. Preliminary studies targeting precipitation of the $NO_3^-$ salts of [Sr(DtBuCH18C6)]$^{2+}$ from isopropyl alcohol were unsuccessful, probably due to a combination of factors including the limited solubility of $Sr(NO_3)_2$ in isopropyl alcohol and the high polarity, dielectric constant, and hydrogen bonding properties of this solvent that serve to keep the $NO_3^-$ complex of [Sr(DtBuCH18C6)]$^{2+}$ in solution (even after the addition of copious quantities of n-heptane).

As a result of these solubility issues, investigations migrated toward the use of less polar etheric and aromatic solvents. Studies using glyme or toluene showed that the $NO_3^-$ salt of [Sr(DtBuCH18C6)]$^{2+}$ did not precipitate from these solvents as well defined solids amenable to recrystallization procedures. Furthermore, dissolution of these $NO_3^-$ complexes proved to be difficult, which hampers $Sr^{2+}$ stripping and the ultimate recovery of purified DtBuCH18C6.

Conversely, $SrCl_2$ is readily dissolved by solutions of DtBuCH18C6, and the resulting complexes could be conveniently suspended in MIBK to facilitate $Sr^{2+}$ removal prior to recovery of purified DtBuCH18C6. Dissolution of DtBuCH18C6 Batch 512 in glyme and contact with a 90 percent stoichiometric quantity (relative to DtBuCH18C6) of solid $SrCl_2.6H_2O$ followed by cooling to 8($\pm$1)° C., isolation and washing of the precipitate, and removal of $SrCl_2$ by stripping in an MIBK/aqueous $Na_2SO_4$ liquid/liquid distribution system provided 96.5 percent pure DtBuCH18C6.

Figure 6A:
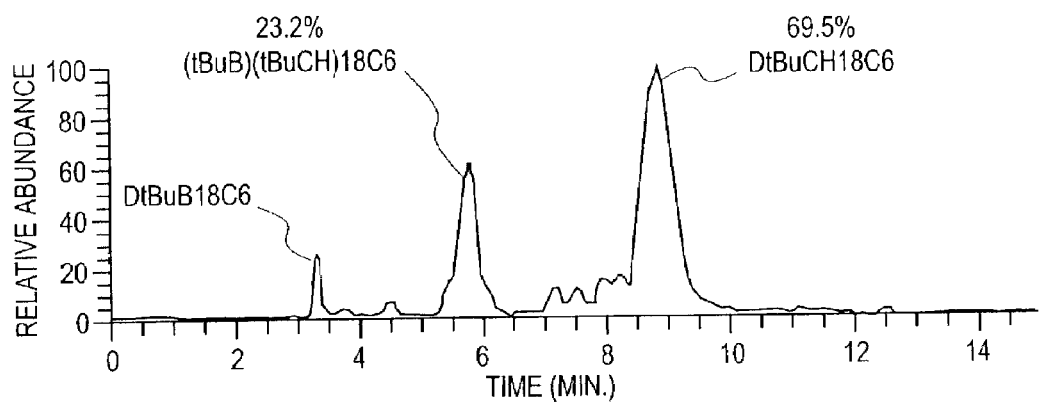
FIG. 6 in two panels shows a RPLC-MS chromatogram of Batch 512 of DtBuCH18C6 extractant showing the materials present and their approximate elution times for the unpurified extractant (FIG. 6A) and a similar chromatogram for the extractant purified by $SrCl_2$ complex precipitated from glyme (FIG. 6B) as described herein.
Figure 6B:
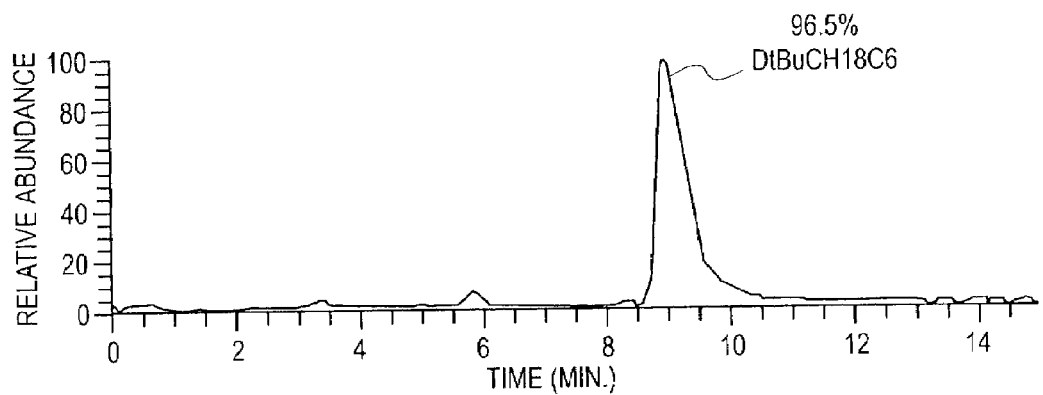
Figure 7A:
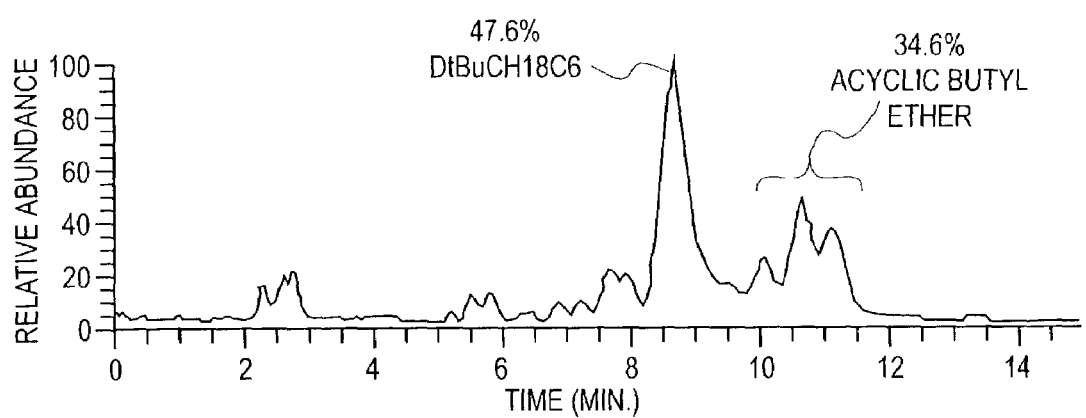
FIG. 7 in two panels (FIGS. 7A and 7B) shows RPLC-MS chromatograms of Batch 527 of DtBuCH18C6 extractant purified by $SrCl_2$ complex precipitation as discussed for FIG. 6.
Figure 7B:
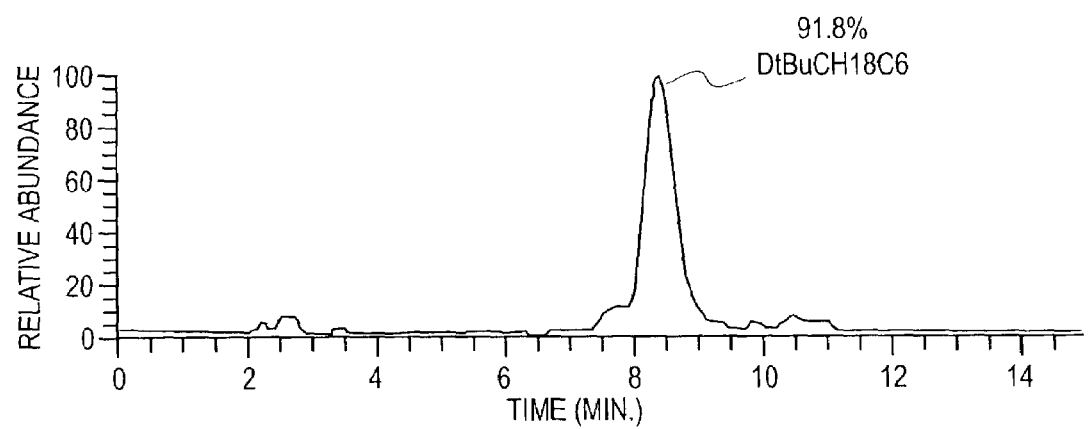

As shown in the lower panel of FIG. 6, DtBuCH18C6 can be effectively separated from the byproducts of incomplete hydrogenation; however, Batch 512 contains only two of the potential impurities that are shown in FIG. 2. A precipitation study was carried out using Batch 527 that contains the ring-substituted acyclic butyl ether to assess the versatility of this method. The chromatogram of FIG. 7 shows an enrichment of DtBuCH18C6 from 47.6 percent to 91.8 percent with a commensurate decrease in the ring-substituted acyclic butyl ether content from 34.6 percent to less than 5 percent.

Unfortunately, the low yield (less than 30 percent) of the glyme precipitation process and the dependence of yield on the type and concentration of impurities forced a continued search for other solvents from which the Sr complex of DtBuCH18C6 could be more efficiently precipitated. Toluene was examined in an attempt at improving the recovery yield of DtBuCH18C6, and FIG. 8 shows a chromatogram of the results of a contact of DtBuCH18C6 Batch 574 with $SrCl_2.6H_2O$ in toluene.

Figure 8A:
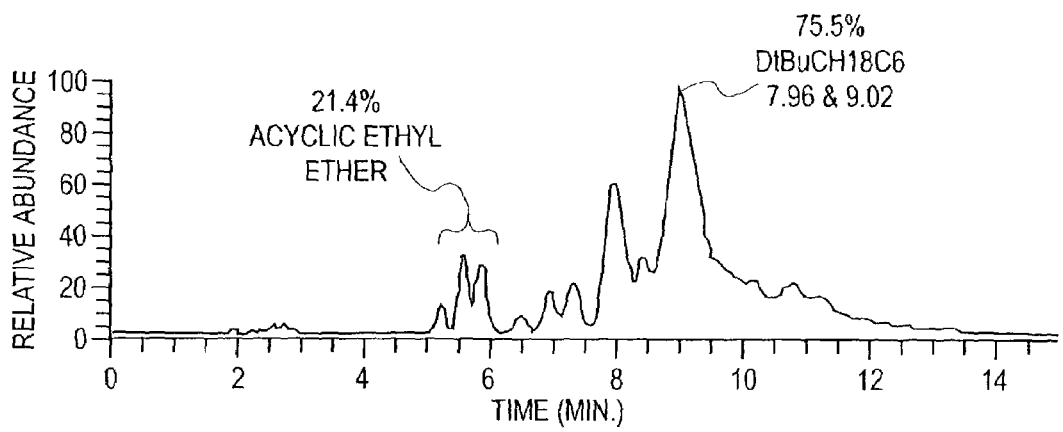
FIG. 8 in three panels shows RPLC-MS chromatograms of Batch 574 of DtBuCH18C6 extractant (FIG. 8A) having a $D_{Sr}$ value of 2.5, DtBuCH18C6 purified by precipitation from toluene with $SrCl_2$ (FIG. 8C) to provide a $D_{Sr}$ value of 4.3, and the toluene supernatant layer after the precipitation (FIG. 8B)
Figure 8B:
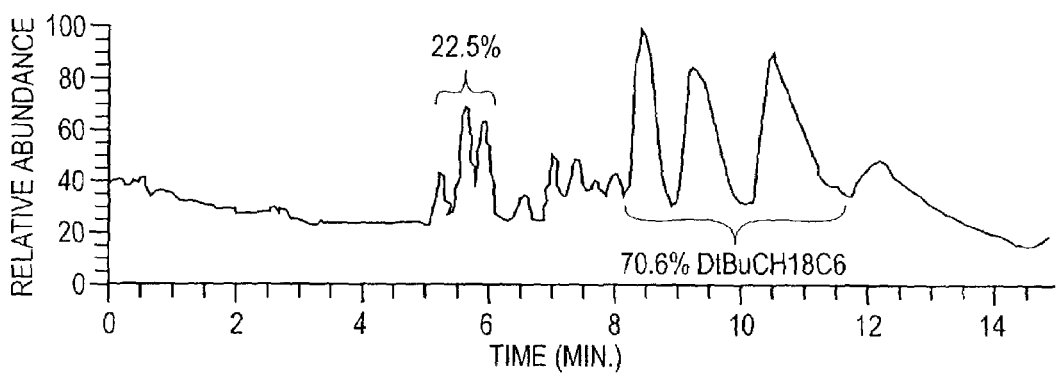
Figure 8C:
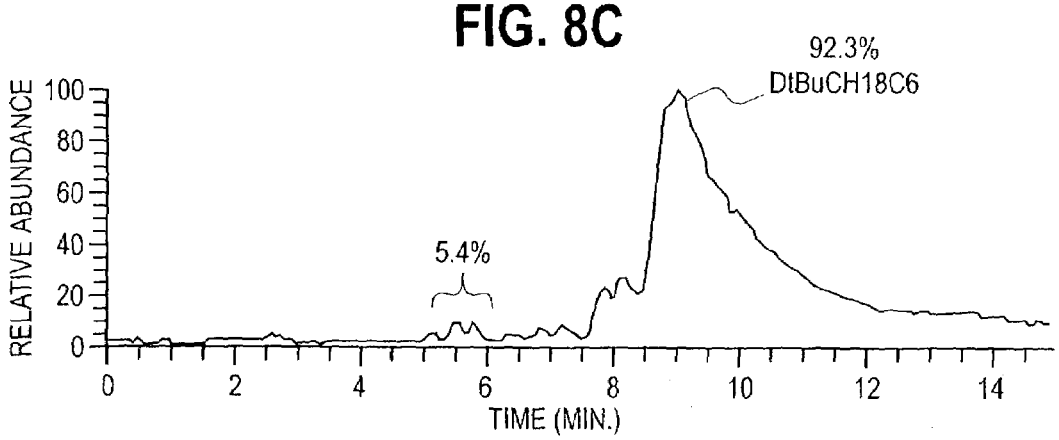

The top panel of FIG. 8 shows that a significant amount of the ring-substituted acyclic ethyl ether is present in the untreated material, along with several peaks in the 7.96–9.02 minute elution range that correspond to DtBuCH18C6 (based on the mass spectral results). As a result of these impurities, the untreated sample exhibited a substandard $D_{Sr}$=2.5.

The middle panel of FIG. 8 shows that the ring-substituted acyclic ethyl ether content remains approximately constant in the toluene supernatant and that three peaks corresponding to DtBuCH18C6 appear in the 8.53–10.58 minute elution range in the chromatogram. The reversed phase liquid chromatography-mass spectrometry (RPLC-MS) assay of the solid that was precipitated, filtered, washed, and stripped of $SrCl_2$ is shown in the lower panel of FIG. 8, where it is seen that the amount of the ring-substituted acyclic ethyl ether impurity has been reduced from 21.4 percent in the untreated sample to 5.4 percent in the purified material. The lower panel also shows that the DtBuCH18C6 content is 92.3 percent after purification (although the very broad band is noted), and that $D_{Sr}$=4.3, which readily exceeds the distribution ratio success criterion.

Figure 9A:
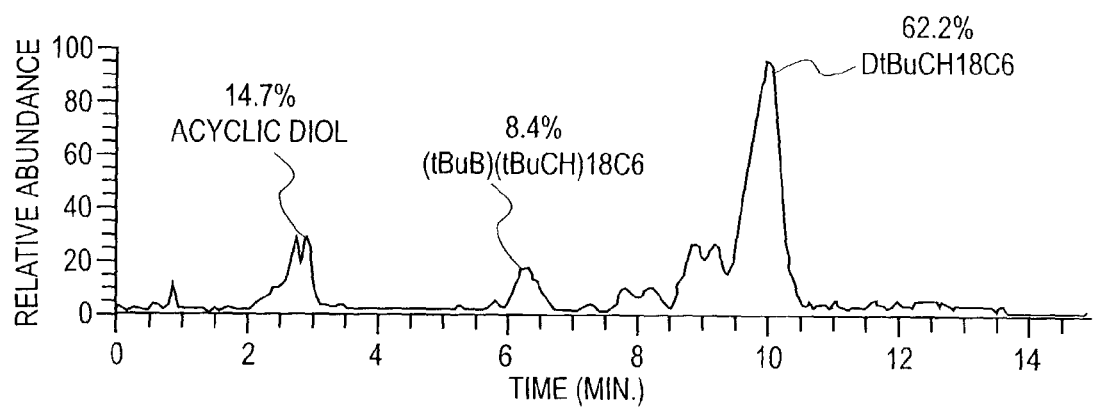
FIG. 9 in two panels shows RPLC-MS chromatograms of Batch 585 of DtBuCH18C6 extractant showing the materials present and their approximate elution times for the unpurified extractant (FIG. 9A) and a similar chromatogram for the extractant purified by precipitation of theDtBuCH18C6/$SrCl_2$ complex from isopropyl alcohol by methyl t-butyl ether (FIG. 9B)

As with the precipitation from glyme, the yields of purified DtBuCH18C6 from toluene never approached the minimum commercial success criterion of 65 percent recovery of 80 percent pure DtBuCH18C6, which prompted testing of an induced precipitation strategy. This technique involves the addition of a less polar solvent (e.g., MTBE) to a solvent (e.g., isopropyl alcohol) in which $SrCl_2$, DtBuCH18C6, and the respective metal complex are readily soluble. Such an approach serves to reduce the polarity, dielectric constant, and solvating properties of the isopropyl alcohol medium to effect precipitation of the $Cl^-$ salt of the [Sr(DtBuCH18C6)]$^{2+}$ complex. FIG. 9 shows the chromatogram of a study using this method, and it can be seen that DtBuCH18C6 is enriched from 62.2 percent to 93.1 percent with a substantial decrease to less than 5 percent of the ring-substituted acyclic diol and (tBuB)(tBuCH)18C6 impurities.

Although the precipitation-based purification strategies were shown to provide DtBuCH18C6 of greater than 90 percent purity and having $D_{Sr}$ greater than 3.5 in accord with the commercial success criteria, the yields using these techniques are unpredictable and inadequate for the desired commercial application and the operational procedures are cumbersome and time consuming. More importantly, the extent of complex precipitation and, consequently, the yield of DtBuCH18C6 were found to be highly sensitive to the type and concentration of the various impurities shown in FIG. 2. The results of other precipitation or precipitation-induced purification studies did not produce isolable solids, and only in rare instances did the yields exceed about 30 percent. It thus became apparent that a more convenient and robust (i.e., less sensitive to byproduct content) purification technique was needed.

Third phase formation in solvent extraction, primarily relating to organophosphorus extractant systems, has been previously described in detail, [Kertes, In *Solvent Extraction Chemistry of Metals*, McKay et al. Eds.; Macmillan: London, (1965); page 377; Vandegrift, In *Science and Technology of Tributyl Phosphate. Volume I: Synthesis, Properties, Reactions, and Analysis*, Schulz et al. Eds.; CRC Press: Boca Raton, Fla., (1984); Vol. I page 69; Kolarik et al., *Solvent Extr. Ion Exch.* (1988) 6:61–91; and Rao et al., *Solvent Extr. Ion Exch.* (1996) 14:955–993] and only a brief overview of the phenomenon and variables pertinent to the purification of DtBuCH18C6 are presented hereinbelow.

As conventionally practiced, solvent extraction involves the partitioning of a solute between two heterogeneous phases, one of which is aqueous and most frequently another that is organic. [Kertes, In *Solvent Extraction Chemistry of Metals*, McKay et al. Eds.; Macmillan: London, (1965); Sekine et al., *Solvent Extraction Chemistry*; Marcel Dekker: New York, 1977; and Rydberg et al. Eds., *Principles and Practices of Solvent Extraction*; Marcel Dekker: New York, 1992.] When an extractant is used in a nonpolar organic diluent and high solute loading is achieved, the extractant/solute species can become insoluble in the organic diluent and can thus separate into a heavy organic phase that is rich in the extractant/solute species and a light organic phase that is depleted of the extractant and solute. When water (or acid), diluent, extractant, and solute are present in sufficient quantities, three phases can form: one that is primarily aqueous, and two that are primarily organic. In a chemical sense, third phase formation is generally attributed to changes in the solubility (or affinity for another phase) of the extractant/solute species.

The third phase formation phenomenon is sensitive to the following variables:

(1) Type and concentration of extractant (e.g., acidic, basic, and neutral extractants have different extraction mechanisms and therefore have different heavy organic phase characteristics);

(2) Diluent polarity and branching (e.g., n-alkane diluents generally form third phases at lower organic phase loadings than do branched alkanes);

(3) Type and concentration of extracted solute (e.g., tri-n-butyl phosphate in n-alkane diluents forms a third phase with tetravalent cations and also with metal-free concentrated acids);

(4) Type and concentration of acid;

(5) Ionic strength of aqueous phase;

(6) Temperature (i.e., the propensity for third phase formation decreases at elevated temperature); and (7) Type and concentration of phase modifier (e.g., alcohols and other polar compounds are used to enhance solubility of the extractant/solute species in the loaded organic phase).

Third phase formation is generally perceived as problematic in solvent extraction as most contacting equipment is not designed to operate with more than two phases; the separation efficiency is degraded; losses of extractant, diluent, and target solute are costly; and solvent extraction plant operations are interrupted. For these reasons, many variables cited above are adjusted to prevent third phase formation, and only infrequently has the formation of a heavy organic phase been induced to accomplish a specific task such as extractant purification. The work described here employs third phase formation with the express intent of purifying an organic extractant such DtBuCH18C6 from its various reaction (here, hydrogenation) byproducts.

A typical third phase formation study involves dilution of as-hydrogenated DtBuCH18C6 to about 1.4 M in a nonpolar organic diluent and contact with a 90 percent stoichiometric quantity of $SrCl_2$ in 3–6 M HCl. After contact and centrifugation, the upper light organic and aqueous phases are separated from the lower, viscous heavy organic phase. The heavy organic phase is then suspended in MIBK (a polar diluent less susceptible to third phase formation than nonpolar diluents), and the $SrCl_2$ is stripped from the organic phase by two contacts with $H_2O$, a single contact with $Na_2SO_4$, and two more contacts with $H_2O$. Details of these manipulations are presented elsewhere herein, and an optimized method for large-scale purification (i.e., greater than 100 g quantities) of DtBuCH18C6 is described below.

Preliminary studies using DtBuCH18C6 Batch 512 in toluene exhibited a heavy organic phase when contacted with a 90 percent stoichiometric quantity of $SrCl_2$ in 3.0 M HCl. The results of this study are shown in the chromatograms of FIG. 10, where the upper panel shows the untreated starting material, the center panel shows the composition of the toluene light organic phase, and the lower panel shows 95.8 percent pure DtBuCH18C6.

The virtually complete rejection of DtBuB18C6 and (tBuB)(tBuCH)18C6 from the heavy organic phase product was a particularly remarkable result that clearly warranted reproducibility testing with other batches of as-hydrogenated DtBuCH18C6. (Recall that the precipitation-based purification methods were highly sensitive to batch variations in the type and concentration of impurities.)

Figure 10A:
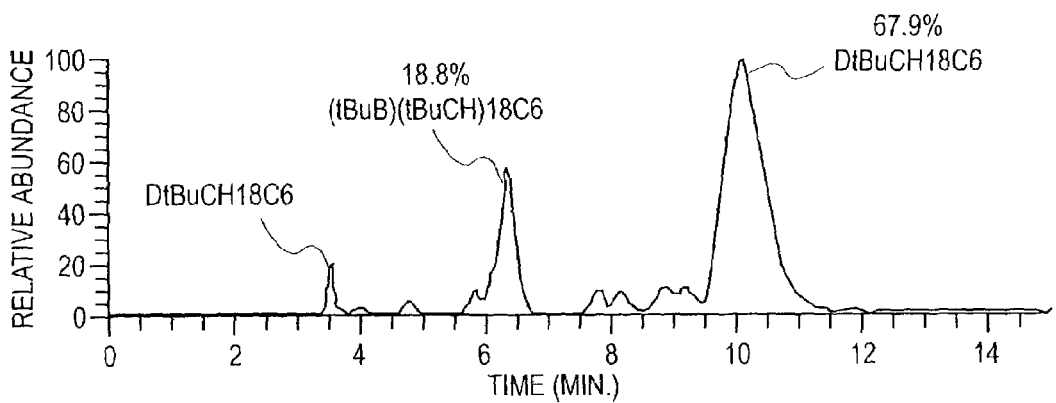
FIG. 10 in three panels shows RPLC-MS chromatograms of Batch 512 of DtBuCH18C6 extractant as unpurified extractant in toluene (FIG. 10A), as a heavy third phase formed using toluene as diluent and an aqueous phase containing SrCl$_2$ in 3.0 M HCl (FIG. 10C), and the also formed toluene light organic phase (FIG. 10B)
Figure 10B:
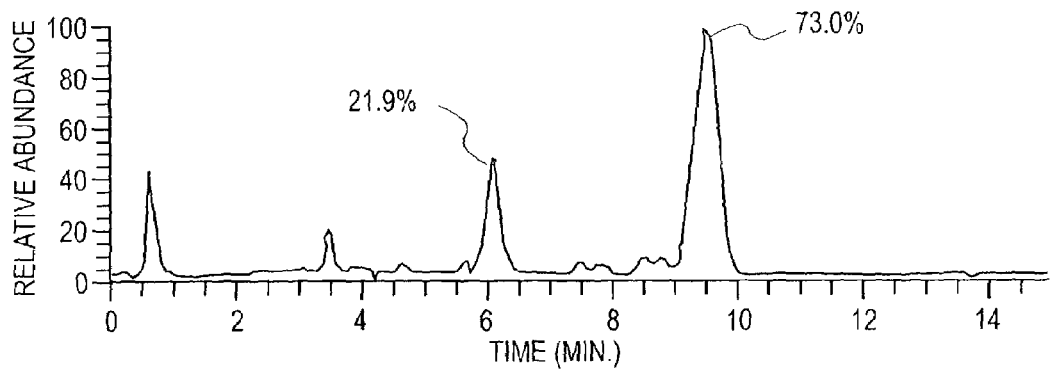
Figure 10C:
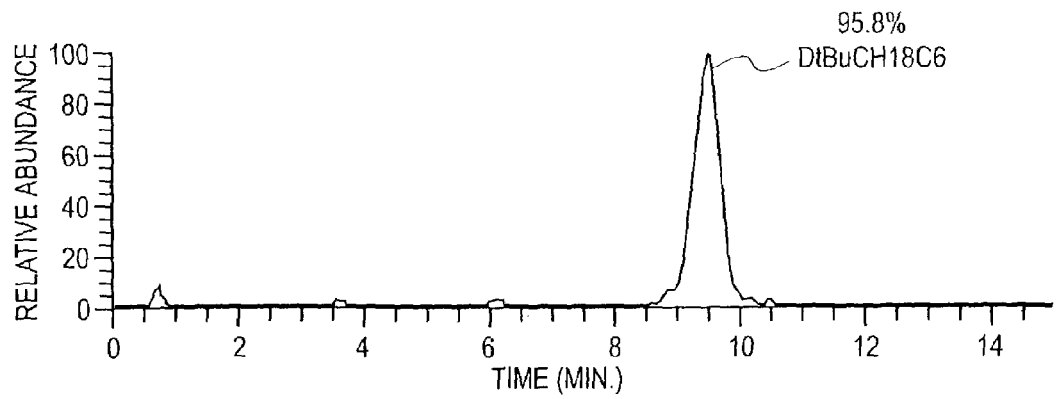
Figure 11A:
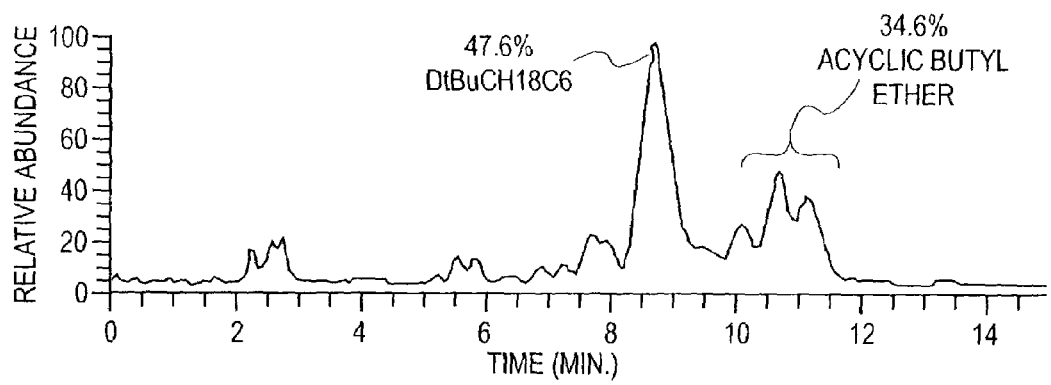
FIG. 11 in three panels shows RPLC-MS chromatograms of Batch 527 of DtBuCH18C6 extractant purified by third phase formation as discussed for FIG. 10 in which the untreated extractant (FIG. 11A) exhibited a D$_{Sr}$ value of 2.5 and the extractant purified using third formation (FIG. 11C) exhibited a D$_{Sr}$ value of 4.6.
Figure 11B:
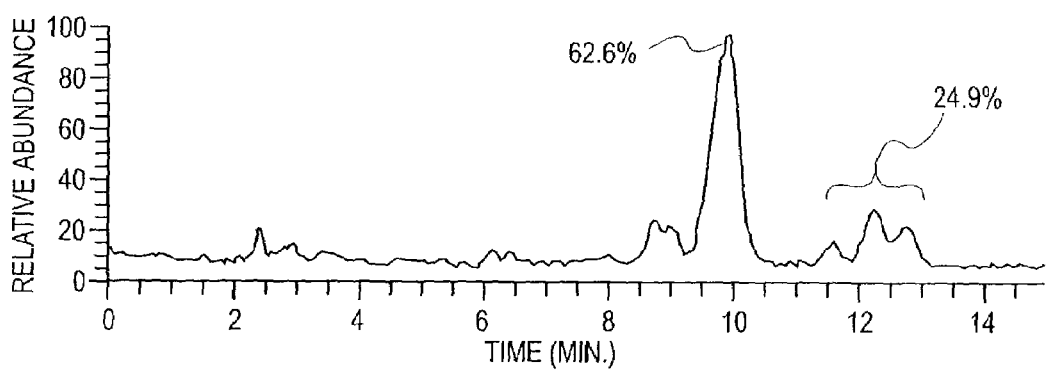
Figure 11C:
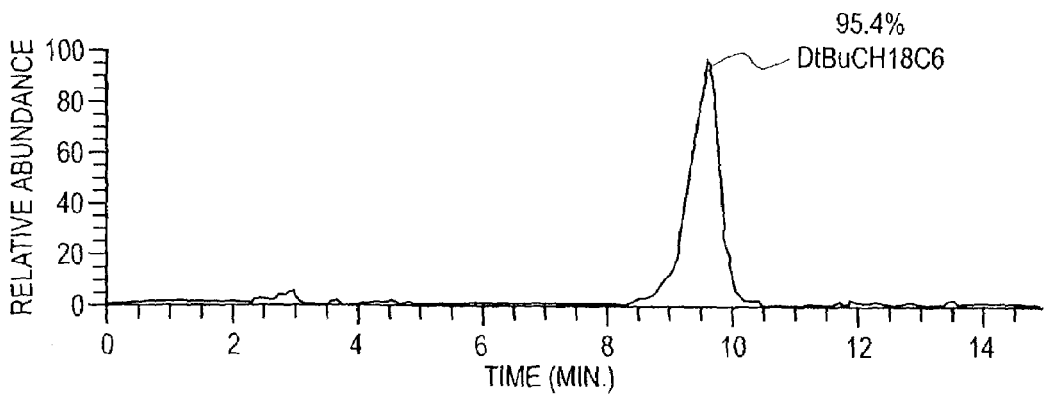

The chromatograms of FIG. 11 depict data similar to those of FIG. 10, and show a rather impressive enrichment of DtBuCH18C6 from a 47.6 percent mixture with the ring-substituted acyclic butyl ether to 95.4 percent after purification. There is a shift in elution times of about 1 minute for the various peaks attributable to DtBuCH18C6, which is most likely attributable to the chromatographic variables discussed in the Analysis section. Also derived from the studies in FIG. 11 are the values of $D_{Sr}=2.5$ for the untreated material and of $D_{Sr}=4.6$ after purification by third phase formation. Of equal importance is that FIGS. 10 and 11 suggest that third phase formation appears to be less susceptible to the batch variations in type and concentration of impurities than the precipitation-based techniques.

Figure 12A:
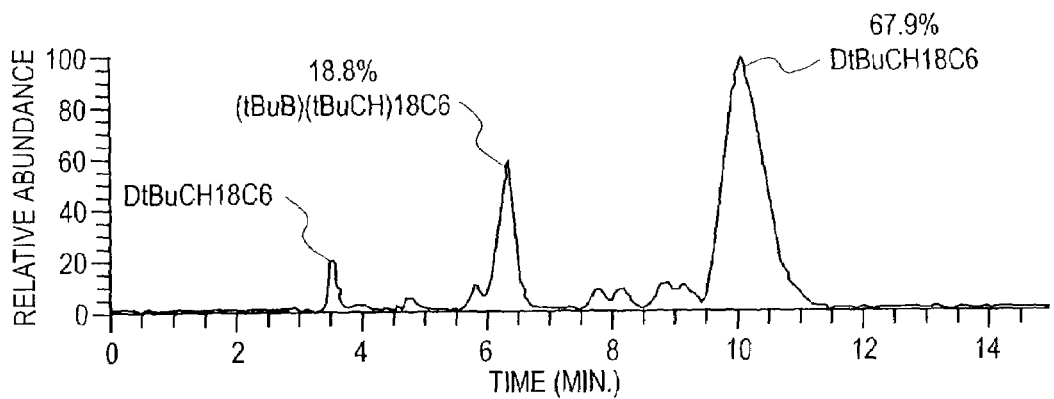
FIG. 12 in three panels shows RPLC-MS chromatograms of Batch 512 of DtBuCH18C6 extractant as discussed for FIG. 10 in which the untreated extractant (FIG. 12A) was purified by third phase formation using both toluene (FIG. 12B) and n-heptane (FIG. 12C) to provide yields of 30.2 percent and 38.9 percent, respectively.
Figure 12B:
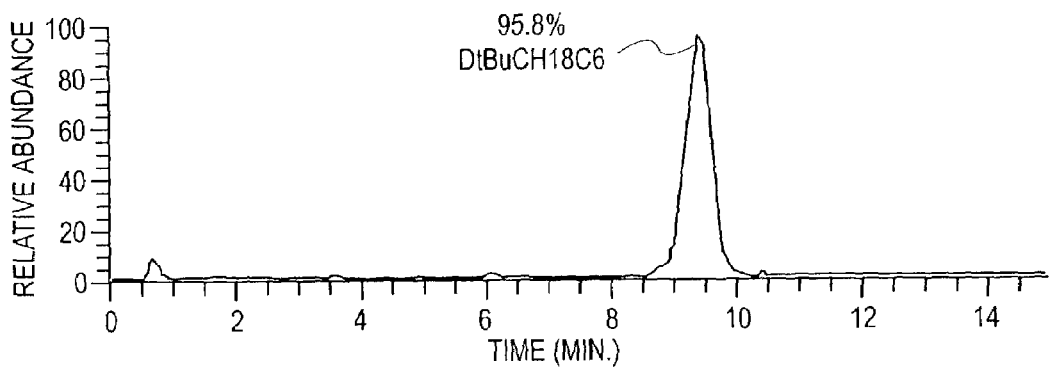
Figure 12C:
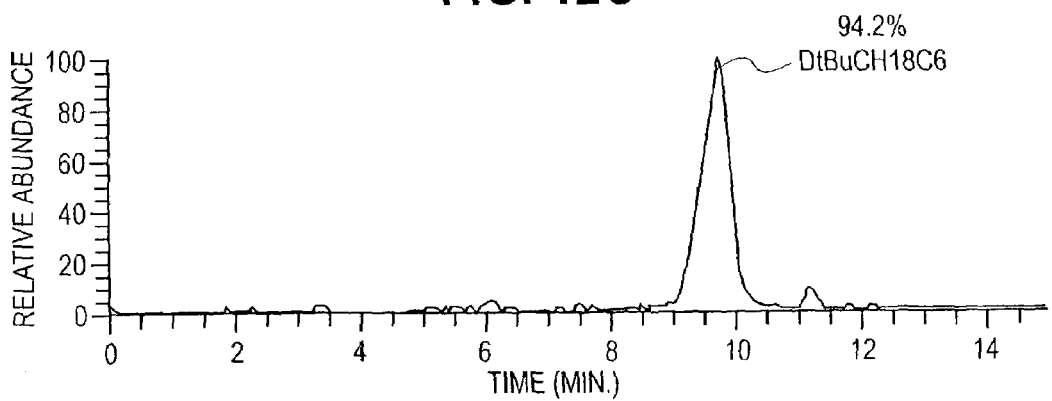
Figure 13A:
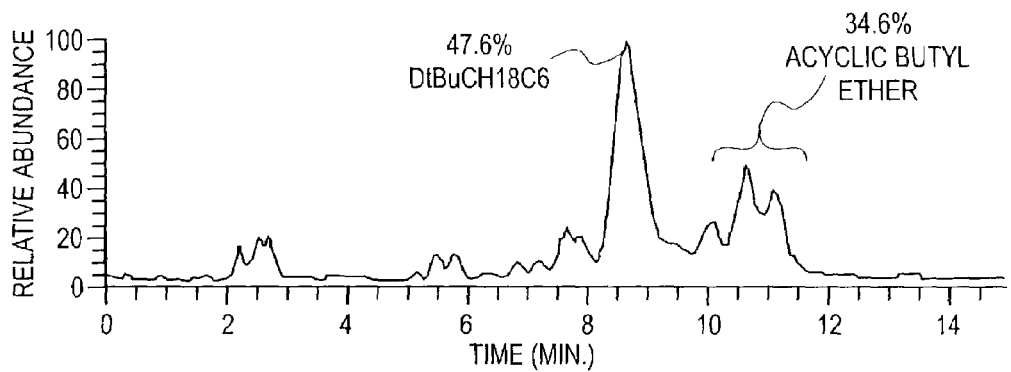
FIG. 13 in three panels shows RPLC-MS chromatograms of Batch 527 of DtBuCH18C6 extractant as discussed for FIG. 10 in which the untreated extractant (FIG. 13A) was purified by third phase formation using both toluene (FIG. 13B) and n-heptane (FIG. 13C) to provide yields of 32.9 percent and 39.1 percent, respectively.
Figure 13B:
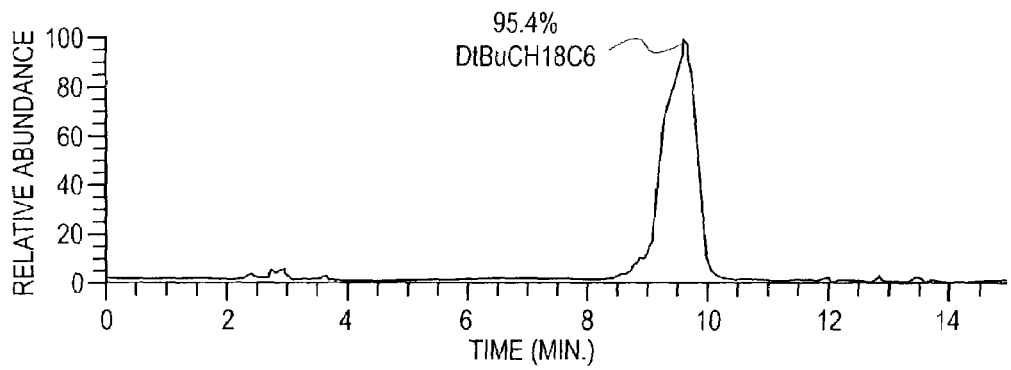
Figure 13C:
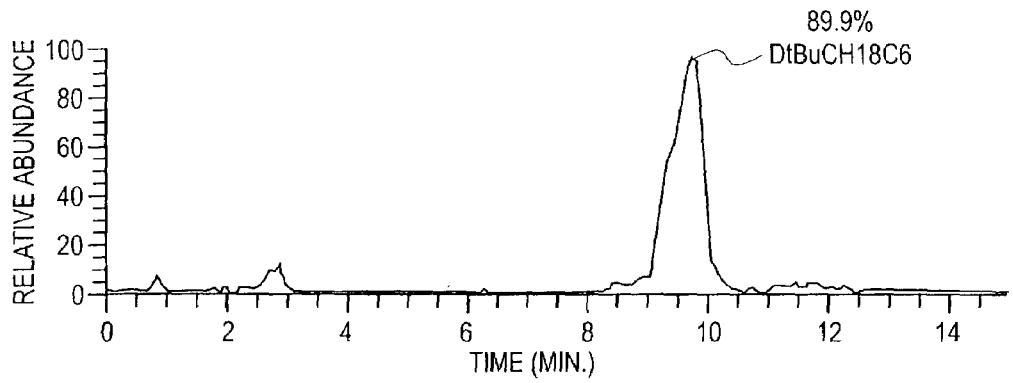
Figure 14A:
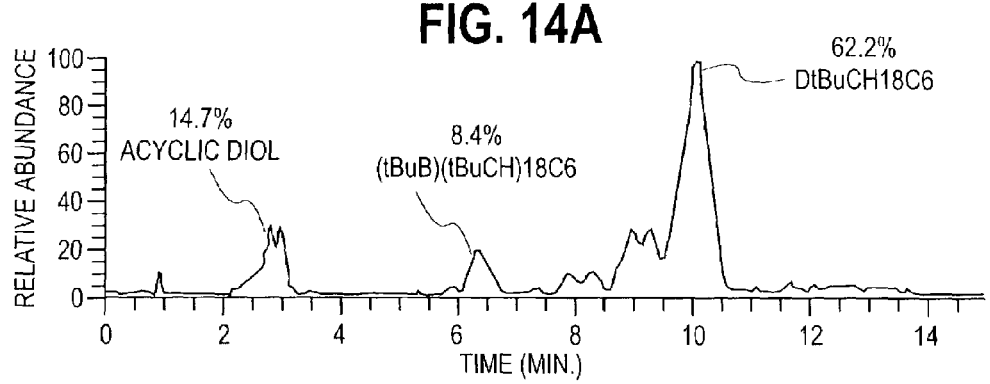
FIG. 14 in three panels shows RPLC-MS chromatograms of Batch 585 of DtBuCH18C6 extractant as discussed for FIG. 10 in which the untreated extractant (FIG. 14A) was purified by third phase formation using toluene (FIG. 14B), and n-heptane (FIG. 14C), and n-dodecane (FIG. 14D) to provide yields of 32.6 (±2) percent, 52 (±7) and 70.5 percent, respectively.
Figure 14B:
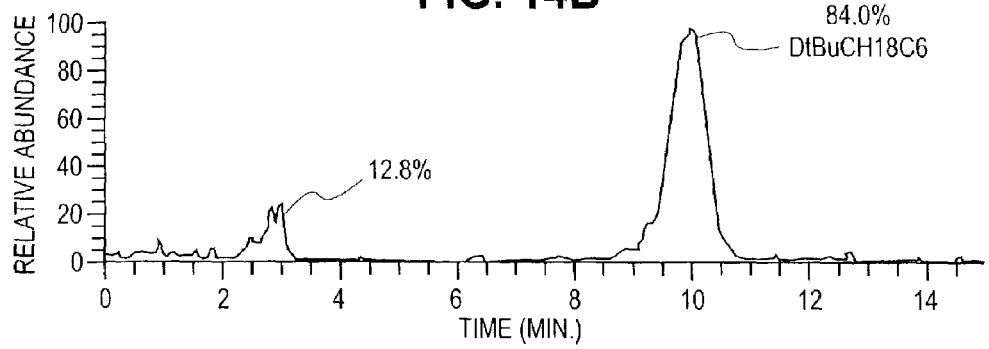
Figure 14C:
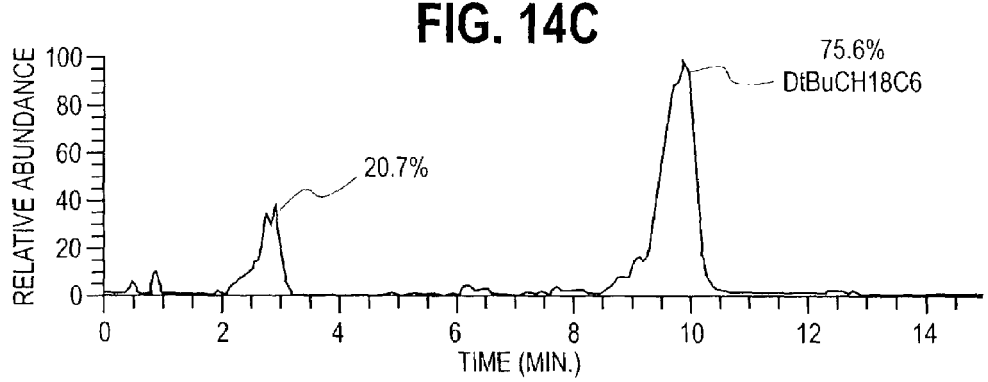
Figure 14D:
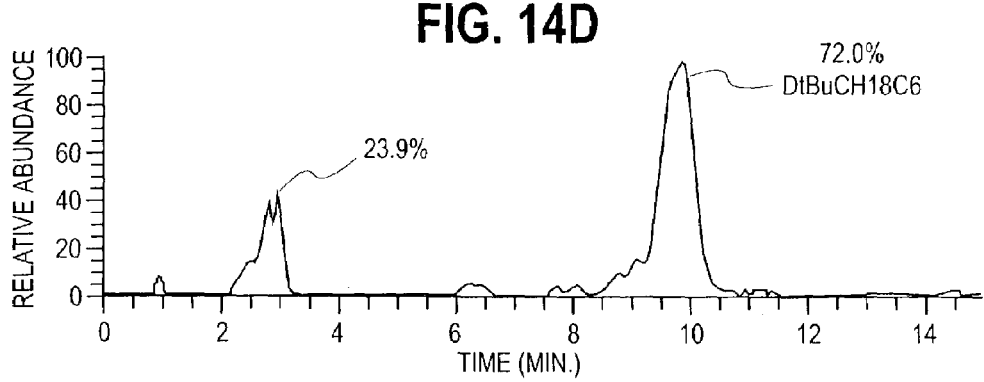

FIGS. 12 and 13 illustrate chromatograms from the purification of two different batches of DtBuCH18C6 by third phase formation using toluene (FIGS. 12B and 13B) or n-heptane (FIGS. 12C and 13C) as diluent, with both yielding equal to or greater than 90 percent pure DtBuCH18C6. The most notable difference between use of these diluents is found in the yields of the DtBuCH18C6 product: average recoveries from n-heptane of 39.0 percent are about 7.5 percent higher than those of 31.6 percent from toluene.

FIG. 14 shows a chromatogram from a more detailed diluent study performed on DtBuCH18C6 Batch 585 that contains both under-hydrogenation and ring cleavage products. From the three lower panels it is evident that the ring-substituted acyclic diol reports to the heavy organic phase and therefore constitutes a substantial impurity in the product obtained by third phase formation. Fortunately, improvements in the hydrogenation conditions minimize the formation of acyclic byproducts, as shown in the chromatogram from the hydrogenation example depicted in FIG. 4.

The studies in FIG. 14 also show that the yield of DtBuCH18C6 increases on going from toluene (32.6(2) percent) to n-heptane (52(7) percent) to n-dodecane (70.5 percent) {in agreement with expectations [Kolarik et al., *Solvent Extr. Ion Exch.* (1988) 6:61–91 and Rao et al., *Solvent Extr. Ion Exch.* (1996) 14:955–993]}, but with a concomitant decrease in the purity of the DtBuCH18C6 product (FIG. 14). Thus, a balance between yield and purity should be maintained during the purification of DtBuCH18C6 by third phase formation, which is in agreement with previous observations using a $HClO_4$-based purification technique. [Dietz et al., *Sep. Sci. Technol.* (1999) 34:2943–2956.]

Table 1 further illustrates the observed inverse relationship between purity and yield, and also shows that the yields for normal vs. branched octanes are comparable. Based on the results shown FIGS. 12–14 and Table 1, it was concluded that the use of n-heptane as diluent represents an acceptable balance between purity, yield, ease of use (i.e., n-heptane in the heavy organic phase can be readily distilled from the DtBuCH18C6 product), and economics.

TABLE 1

Influence of Diluent on Yield and Purity of DtBuCH18C6 from Batch 585[a] by Third Phase Purification

| Diluent | Yield (Percent)[b] | Purity (Percent) |
|---|---|---|
| toluene | 32.4 | 84.0 |
| toluene | 32.8 | 70.9 |
| n-heptane | 58.1 | 75.6 |
| n-heptane | 41.9 | — |
| n-heptane | 55.2 | — |
| n-heptane | 62.9 | — |
| n-octane | 55.2 | — |
| iso-octane (2,2,4-trimethylpentane) | 58.1 | — |
| n-dodecane | 70.5 | 72.0 |

[a]Untreated sample is 62.2 percent DtBuCH18C6.
[b]Yield with respect to $Sr^{2+}$ as the limiting reactant used in the purification.

Figure 15A:
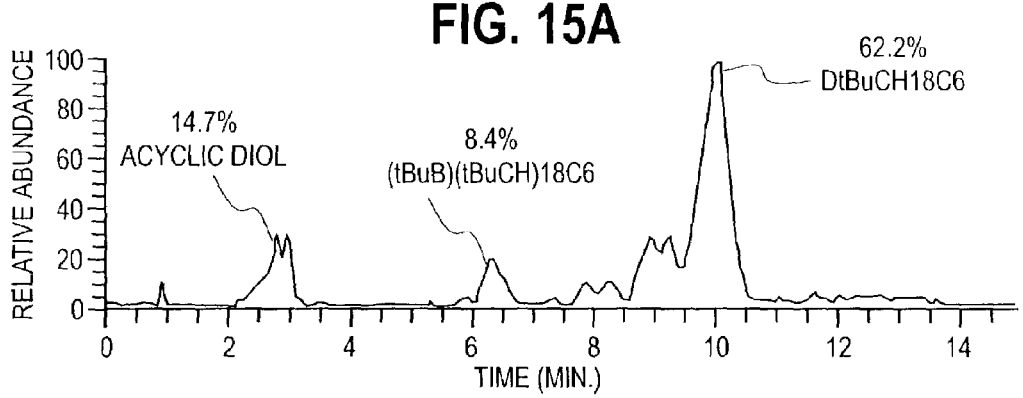
FIG. 15A) or purified by third phase formation that show the effect of HCl concentration using toluene as diluent and an aqueous phase containing SrCl$_2$ in HCl at concentrations of 3.0 M (D$_{Sr}$=3.8, 32.6±2% recovery.
Figure 15B:
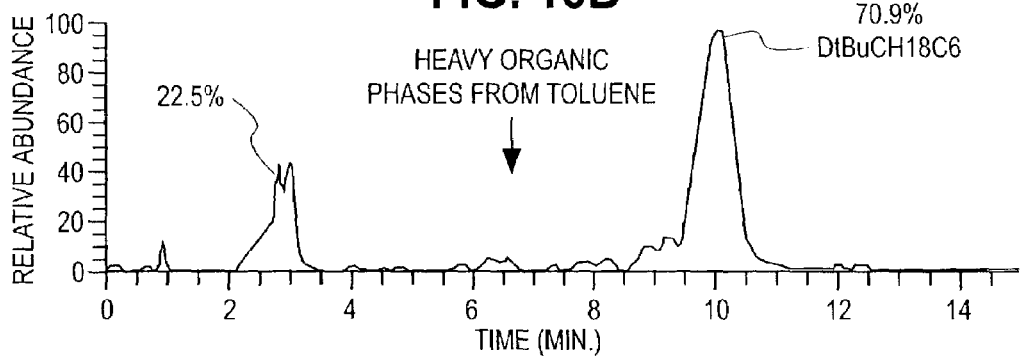
FIG. 15B), 4.5 M (D$_{Sr}$=3.6, 69±1% recovery.
Figure 15C:
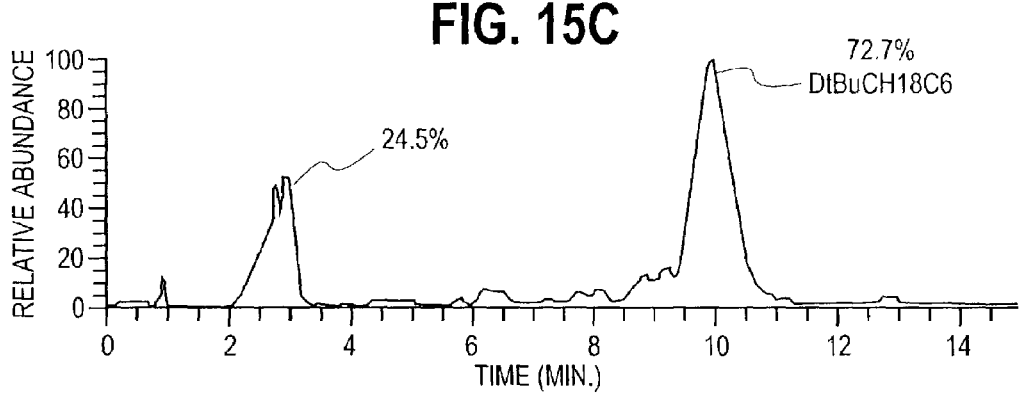
FIG. 15C), and 6.0 M (D$_{Sr}$=3.3, >100% recovery.
Figure 15D:
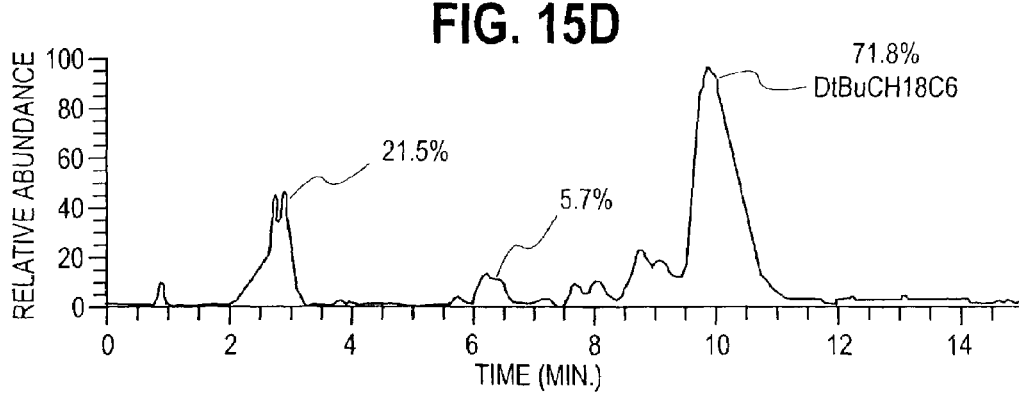
FIG. 15D)
Figure 16A:
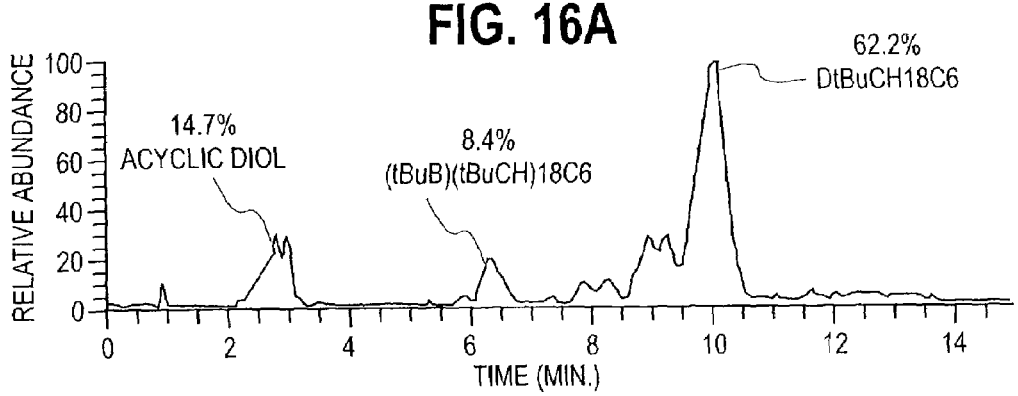
FIG. 16A shows the untreated material.
Figure 16B:
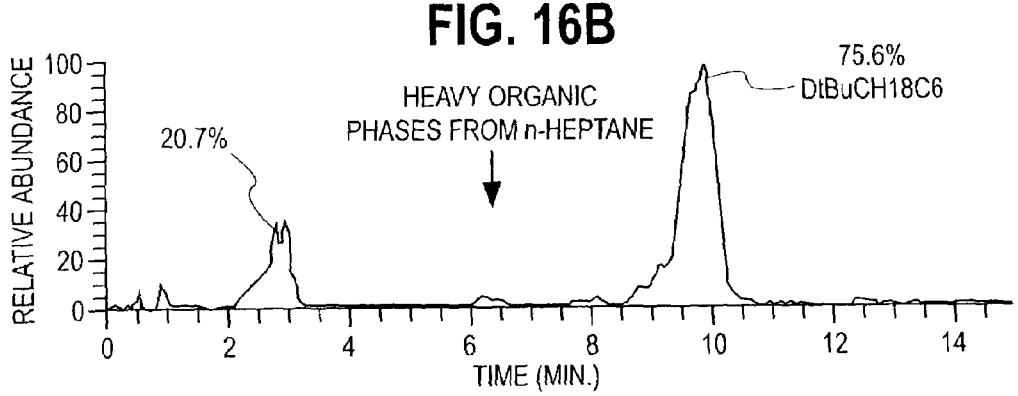
FIG. 16B shows purification from 3.0 M HCl (52±7% recovery)
Figure 16C:
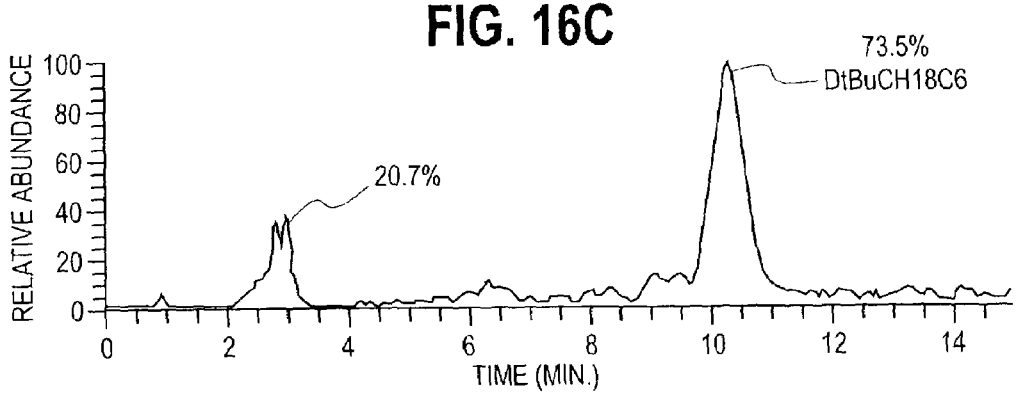
FIG. 16C shows purification from 4.5 M HCl (96.2% recovery)
Figure 16D:
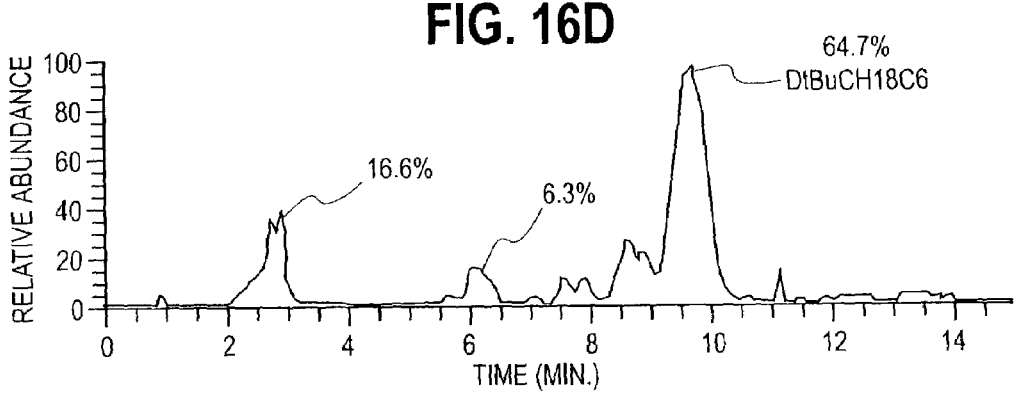
FIG. 16D shows purification from 6.0 M HCl (>100% recovery)

The acidity of the aqueous phase is another variable important in purification by third phase formation that can be conveniently adjusted to maximize the recovery of DtBuCH18C6. The chromatograms of FIG. 15 present data for the purification of DtBuCH18C6 Batch 585 using third phase formation when contacted with 3.0 (FIG. 15B), 4.5 (FIG. 15C) and 6.0 (FIG. 15D) M HCl. The percentage of DtBuCH18C6 in the heavy organic phase increased from 62.2 percent in the untreated material to 70.9, 72.7, and 71.8 percent on increasing the HCl concentration from 3.0, to 4.5, and then to 6.0 M (FIGS. 15B–D), respectively. As observed earlier, the ring-substituted acyclic diol partitions to the heavy organic phase; however, the more frequently encountered (tBuB)(tBuCH)18C6 content is less than 5 percent in 3.0 and 4.5 M HCl, but again significant at 5.7 percent in the sample obtained using a 6.0 M HCl aqueous phase (FIG. 15D).

The most prominent effect of increasing the aqueous phase acidity is in the overall yield of product, with an approximate two-fold increase in yield on going from 3.0 [32.6 (±2) percent] to 4.5 [69 (±1) percent] M HCl. The yield of DtBuCH18C6 product (with respect to $Sr^{2+}$) exceeds 100 percent in 6.0 M HCl due to the combined influence of high solute (i.e., $Sr^{2+}$) loading and high acid concentration, which force the ring-substituted acyclic diol and (tBuB)(tBuCH)18C6 into the heavy organic phase. In general agreement with the decrease of DtBuCH18C6 purity (and increase in byproduct content), $D_{Sr}$ values decrease from 3.8, 3.6, to 3.3 on increasing the HCl concentration used in the purification process from 3.0, 4.5, to 6.0 M, FIGS. 15B–D, respectively. In keeping with the diluent effects studies, aqueous phase acidity should also be adjusted to appropriately balance the inverse relationship between purity and yield of the DtBuCH18C6 product.

The chromatogram panels of FIG. 16 show a similar variation in acid concentration, except that n-heptane was used as the diluent. Again, the purity of DtBuCH18C6 decreases as the HCl concentration increases from 3.0, 4.5, to 6.0 M (FIGS. 16B–D, respectively) due to the increased partitioning of impurities to the heavy organic phase [i.e., ring-substituted acyclic diol+(tBuB)(tBuCH)18C6]. Most striking is the difference in the yields obtained here for n-heptane when compared to yields obtained using toluene. From toluene media, 3.0 M HCl yields 32.6(±2) percent and 4.5 M HCl yields 69(±1) percent, whereas for n-heptane 3.0 M HCl yields 52(±7) percent and 4.5 M HCl yields 96.2 percent.

The data of FIGS. 15 and 16 provide additional evidence that n-heptane is a preferred diluent when yield and purity are of prime concern, and also indicate that about 4.5 M HCl is optimal for these criteria. These conclusions are, however, partially obscured by the presence of the ring-substituted acyclic diol in Batch 585 and its partitioning to the heavy organic phase.

Consequently, DtBuCH18C6 Batch 590-2 was subjected to the same acid dependence studies as Batch 585 (FIG. 16), except that the chromatogram of FIG. 17A shows that Batch 590-2 does not contain ring-substituted acyclic polyethers. The hydrogenation reaction was incomplete for this sample, affording a mixture of 6.8, 41.0, and 47.6 percent DtBuB18C6, (tBuB)(tBuCH)18C6, and DtBuCH18C6, respectively.

Upon increasing the aqueous phase HCl concentration from 3.0 (FIG. 17B) to 4.5 (FIG. 17C) M, the percentage of DtBuCH18C6 in the product derived from the heavy organic phase decreased slightly from 86.3 percent to 79.9 percent, while the (tBuB)(tBuCH)18C6 content remained essentially constant at about 13 percent. Such a decrease in (tBuB)(tBuCH)18C6 content from the original 41.0 percent to about 13 percent in the heavy organic phase is notable, as the under-hydrogenation products are presently the most frequently encountered byproducts in as-hydrogenated DtBuCH18C6. As observed for Batch 585, 6.0 M HCl (FIG. 17D) caused most of the impurities to partition to the heavy organic phase; consequently, this HCl concentration is not a candidate for commercial use.

The yields of DtBuCH18C6 from Batch 590-2 are substantially lower than observed for Batch 585 (FIG. 16); however, the additional 7–10 percent purity of the products derived from Batch 590-2 compensates somewhat for the lower yield. The chromatograms of FIGS. 16 and 17 further underscore the impact of batch variations of impurity type and concentration on recoveries and purity of the purified products.

The procedures discussed above have utilized those variables affecting third phase formation that are most conveniently adjusted (i.e., diluent and acid concentration) to provide DtBuCH18C6 according to certain success criteria. Several of the remaining variables pertinent to third phase formation have been examined, but certain variables have not been tested. For example, a more dilute solution of as-hydrogenated DtBuCH18C6 could be used prior to third phase formation, but the concentration of the hydrogenation reaction product was not examined as the objective of this work is to develop a versatile, commercially viable process affording high yields of pure DtBuCH18C6. The work reported here uses about 1.4 M untreated DtBuCH18C6 for third phase formation, which is just dilute enough to reduce the viscosity of the untreated material so that adequate phase dispersion is achieved for the solvent extraction reaction yet is concentrated enough to produce a heavy organic phase in good yield.

The majority of the studies discussed here have used $SrCl_2$ extraction to introduce some measure of selectivity into the purification process because it is known that certain stereoisomers of DtBuCH18C6 exhibit superior extraction of $Sr^{2+}$, whereas the various reaction byproducts and the remaining stereoisomers are far less efficient $Sr^{2+}$ extractants. [Hay et al., RL3-6-C3-31; Pacific Northwest National Laboratory; Richland, Wash., 1996 and Hay, In *Metal-Ion Separation and Preconcentration: Progress and Opportunities*; Bond et al. Eds., American Chemical Society: Washington, D.C., 1999; Vol. 716:102–113.] As a test of this hypothesis, studies in which third phase purification was attempted in the absence of $SrCl_2$ were performed.

Figure 18A:
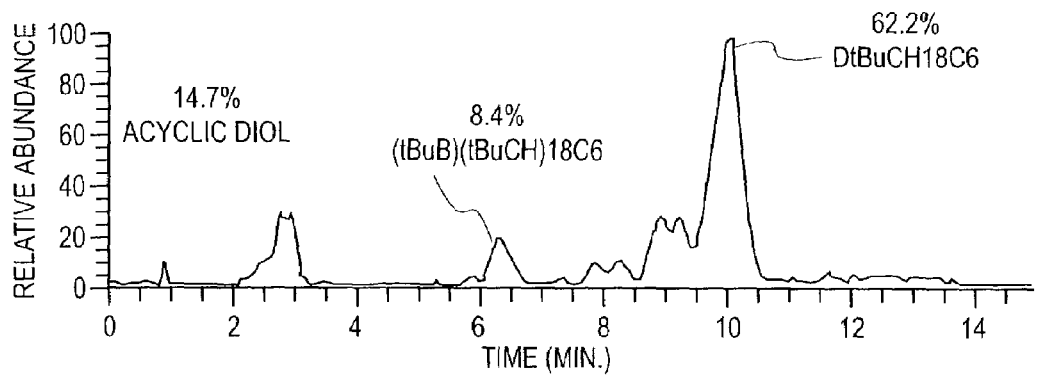
FIG. 18 in five panels shows RPLC-MS chromatograms of Batch 585 of DtBuCH18C6 extractant as an unpurified extractant (FIG. 18A) and the materials obtained by third phase formation using n-heptane as diluent in the presence of 4.5 M HCl with no added metal ion (FIG. 18B), or 0.9 M metal chloride in 4.5 M HCl using KCl (>100%.
FIG. 18C), SrCl$_2$ (96.2%.
FIG. 18D) and LaCl$_3$ (>100%.
FIG. 18E).
Figure 18B:
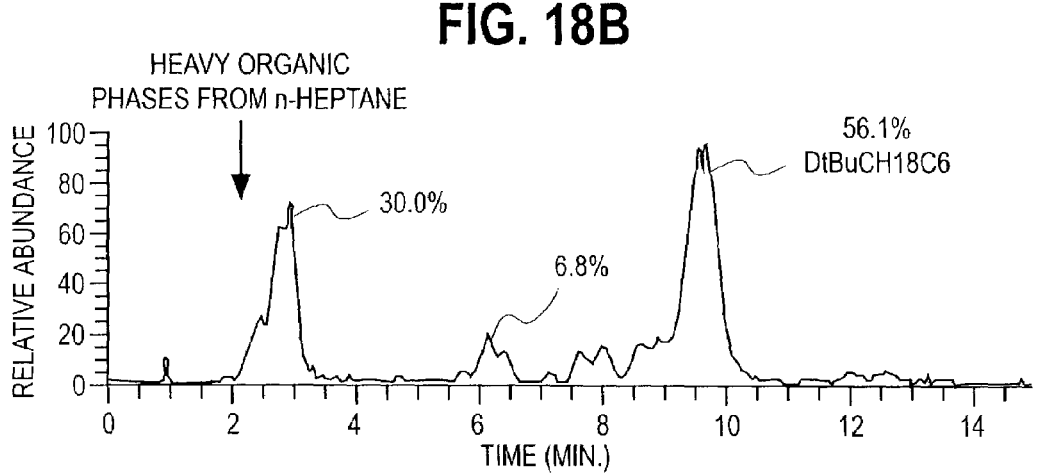
Figure 18C:
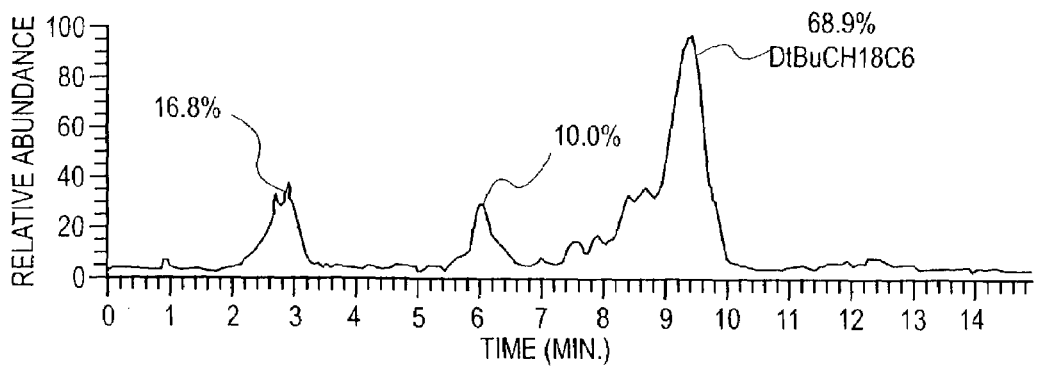

Use of 3.0 M HCl does not form a heavy organic phase from toluene or n-heptane solutions of DtBuCH18C6, but 4.5 M and 6.0 M HCl both yield heavy organic phases that are less dense than the aqueous phase. There are no statistically significant differences between the RPLC-MS chromatograms of the heavy organic phases from 4.5 M HCl (FIG. 18B) and 6.0 M HCl, and neither shows enrichment of DtBuCH18C6. Similarly, the heavy organic phases formed by contact of n-heptane solutions of Batch 585 with 4.5 M solutions of $HNO_3$ or $HClO_4$ free of added metal ions were less dense than the aqueous phase and had ring-substituted acyclic diol, (tBuB)(tBuCH)18C6, and DtBuCH18C6 compositions statistically identical to those obtained from 4.5 M HCl.

Also shown in FIG. 18 are the results of third phase formation studies using KCl, $SrCl_2$, and $LaCl_3$ from n-heptane diluent and 0.9 M metal chloride in 4.5 M HCl (0.9:1 Mn+:DtBuCH18C6). Use of KCl as the extracted solute forms a third phase less dense than the aqueous phase, and little enrichment in DtBuCH18C6 content is observed. Similarly, $LaCl_3$ provided minimal enrichment of DtBuCH18C6 in the heavy organic phase; however, the heavy organic phase formed using this compound was more dense than the aqueous phase, which is suggestive of $La^{3+}$/DtBuCH18C6 interactions.

Figure 18D:
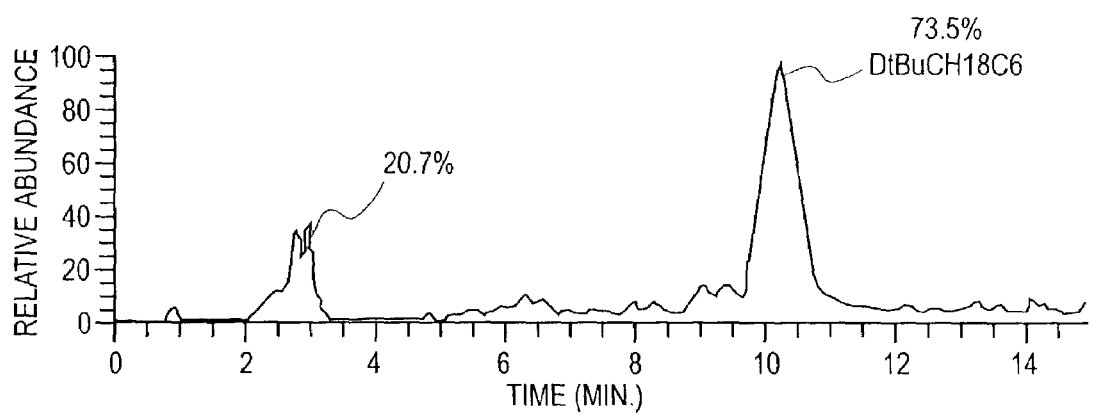
Figure 18E:
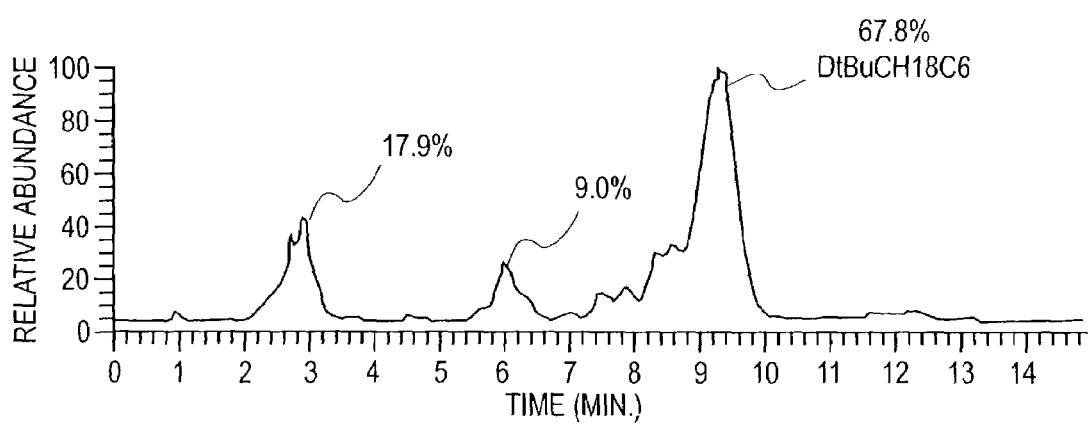
Figure 19A:
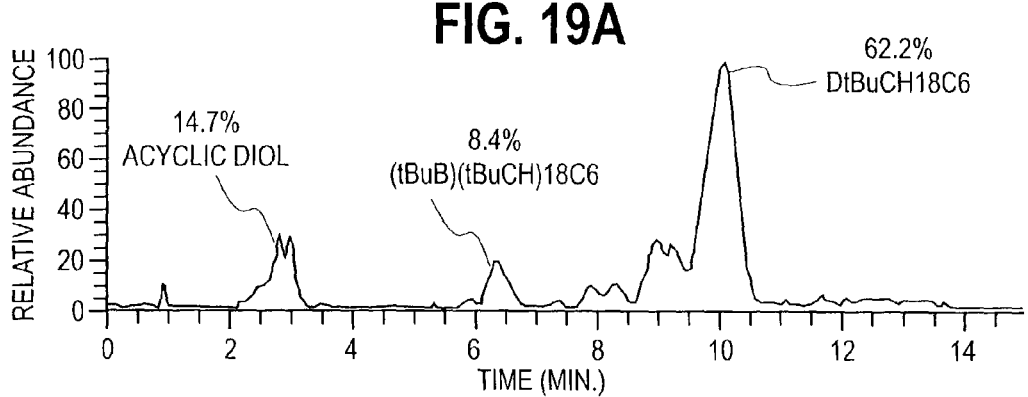
FIG. 19 in four panels shows RPLC-MS chromatograms of Batch 585 of DtBuCH18C6 extractant that illustrate the effects of repeated purification of untreated extractant (FIG. 19A) by third phase formation using a n-heptane diluent and SrCl$_2$ in 4.5 M HCl to provide yield of 89.3% (FIG. 19B), 95.4% (FIG. 19C), and 100% (FIG. 19D)
Figure 19B:
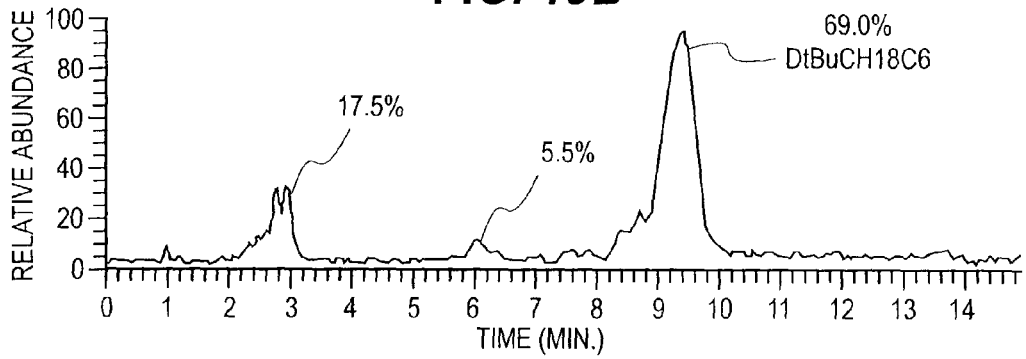
Figure 19C:
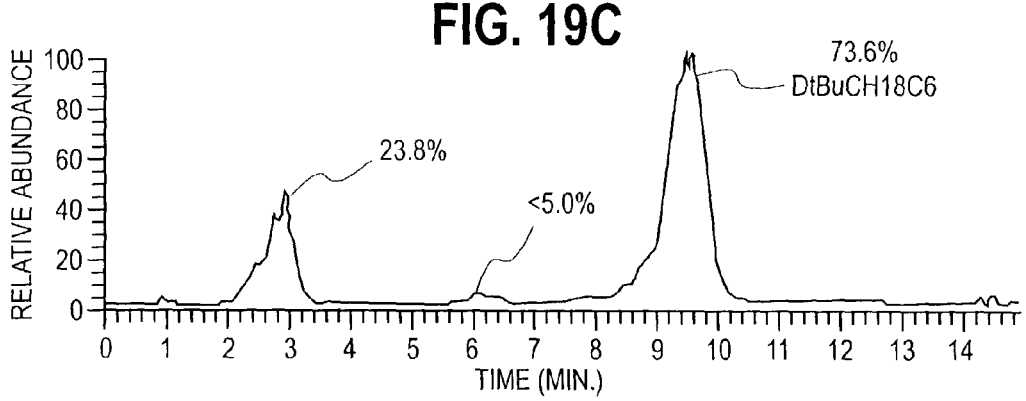
Figure 19D:
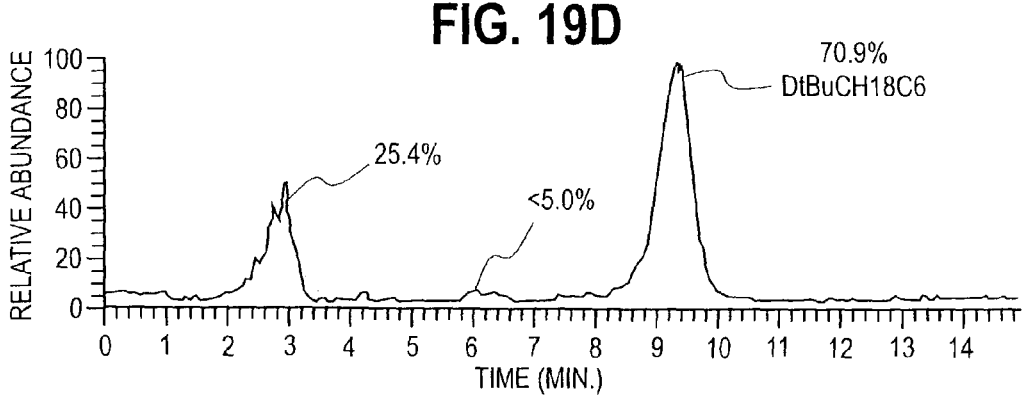

FIG. 18D shows for comparison the product derived from the heavy organic phase formed in the presence of $SrCl_2$, and it is evident that this cation (and probably $Pb^{2+}$) are well suited to the purification of DtBuCH18C6 by third phase formation. Fortuitously, the $Cl^-$ complex of [Sr(DtBuCH18C6)]$^{2+}$ forms a heavy organic phase that is more dense than the light organic and aqueous phases. This density difference is useful because the purified DtBuCH18C6 product in the bottom heavy organic phase does not contact the light organic phase containing the impurities (i.e., they are separated by the aqueous phase), which minimizes contamination and simplifies isolation of the heavy organic phase product.

A limited examination of anion effects on third phase formation was conducted using $Sr(NO_3)_2$ and $Sr(ClO_4)_2$ in 4.5 M solutions of their respective acids. The $NO_3^-$ compounds present solubility issues as mentioned in the discussion of precipitation methods, nevertheless third phases were formed with DtBuCH18C6 Batch 585 (solids, rather than third phases, can form with different batches of DtBuCH18C6). Rather surprisingly, little enrichment of DtBuCH18C6 was exhibited by either the $NO_3^-$ or $ClO_4^-$ systems with DtBuCH18C6 contents of 62.4 percent and 59.3 percent, respectively, which more closely resemble the raw starting material (FIG. 18A) than the material purified by third phase formation using $SrCl_2$ (FIG. 18D). Aside from the solubility properties and convenience of third phase formation using Cl—based systems, it appears that [Sr(DtBuCH18C6)]$^{2+}$ complexes of this anion also provide a higher purity DtBuCH18C6 product.

Studies have also been carried out in which the stoichiometric ratio of $Sr^{2+}$:DtBuCH18C6 was varied. These studies showed an increase in DtBuCH18C6 content of Batch 585 from about 65 percent at a stoichiometry of 0.75:1 to about 74 percent at 0.9:1, after which the percentage of DtBuCH18C6 (and the ring-substituted acyclic diol) plateau through a superstoichiometric ratio of 1.25:1.

The chromatograms of FIG. 19 show the results of the sequential third phase purification of DtBuCH18C6 Batch 585. FIG. 19A shows the untreated material, and the remaining three panels show the analyses of the products obtained from the heavy organic phase after each of three third phase formation processes, respectively. The ring-substituted acyclic diol content increased regularly through the three purification cycles, whereas the (tBuB)(tBuCH)18C6 content decreased to less than 5 percent. After one regimen of third phase formation (FIG. 19B), the DtBuCH18C6 content was increased to about 70 percent, after which the DtBuCH18C6 content was substantially constant through the remaining two purification procedures FIGS. 19C–D).

The most notable effects of repeated purification is the disappearance of the peaks at 8.95 minutes observed in the untreated material (top panel), which correspond to DtBuCH18C6 based on the mass spectral data. The disappearance of these peaks after three cycles of third phase purification (FIG. 19D) and the improved symmetry of the peak at 9.39 minutes suggest that some degree of isomer enrichment is occurring, and the extent of this enrichment is presently under investigation.

Based on the results shown in FIGS. 12–18 and Table 1, n-heptane as diluent and $SrCl_2$ in 4.5 M HCl as the aqueous phase were determined to represent the best balance between purity, yield, ease of use, and economics for the purification of DtBuCH18C6 by third phase formation. Several scale-up studies using these parameters were performed incrementally: 2 g, 6 g, 80 g, and 200 g, with each study showing that both the purity and yield of the DtBuCH18C6 product increased as the effects of losses and contamination due to manipulations, transfers, etc., became less significant as the preparation scale increased.

Figure 20:
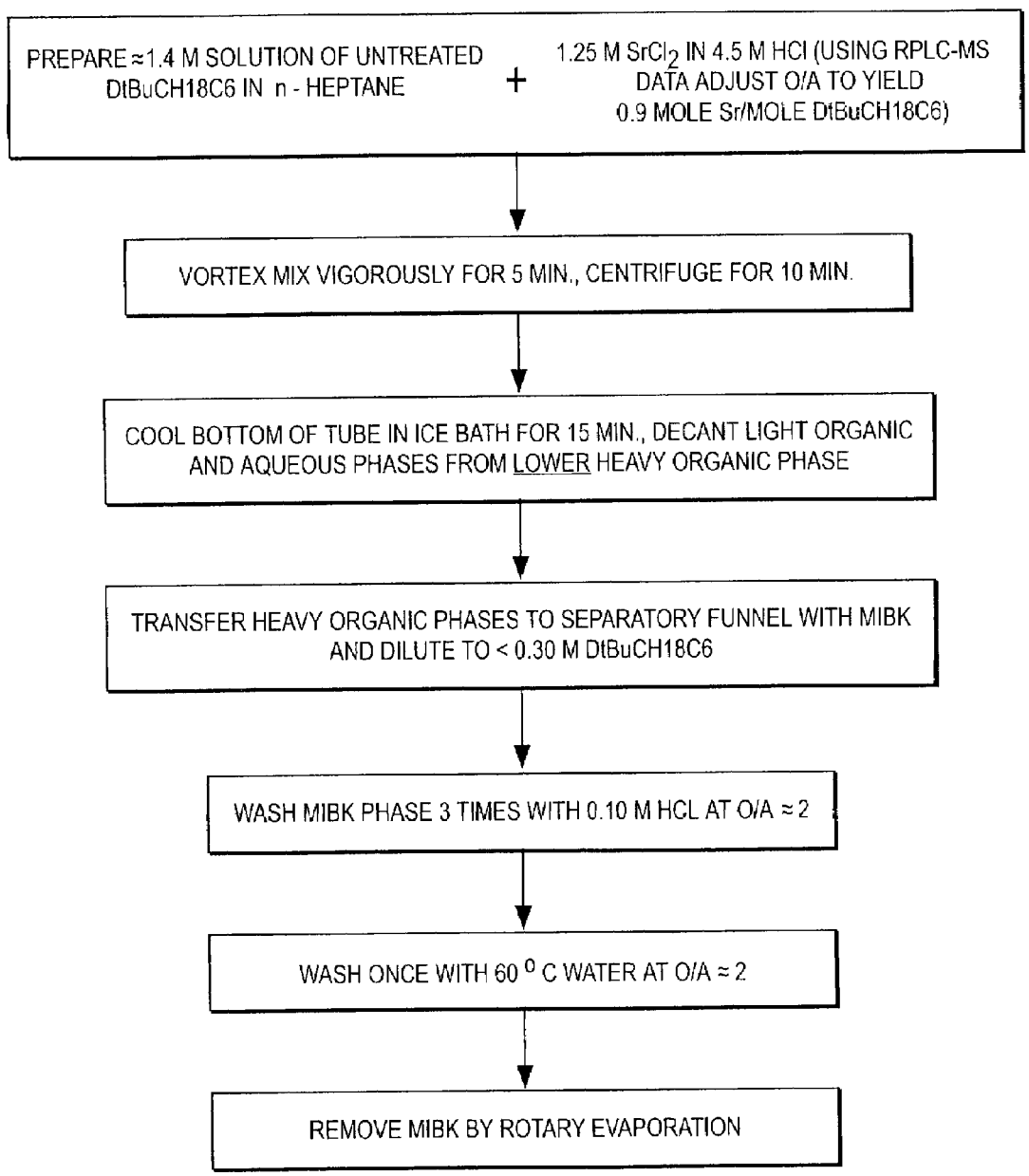
FIG. 20 is an optimized flow-sheet for the purification of greater than 100 g quantities of DtBuCH18C6.

A general flow-sheet for laboratory-scale purification of DtBuCH18C6 is depicted in FIG. 20. By example, a 200 g sample of as-hydrogenated DtBuCH18C6 (+byproducts) is distributed evenly amongst twelve different 50 mL centrifuge tubes, n-heptane is added to provide a solution of about 1.4 M, and the tubes were gently heated in a bath at 60° C. to facilitate dissolution. A sufficient volume of 1.25 M $SrCl_2$ in 4.5 M HCl was added to each tube so that the stoichiometric ratio of $Sr^{2+}$:DtBuCH18C6 was about 0.9:1 (DtBuCH18C6 content of the untreated material previously determined by RPLC-MS). Each tube was vigorously shaken to ensure good phase contact and followed by centrifugation to give three phases from top to bottom: light organic, aqueous, and heavy organic. The bottoms of the 12 centrifuge tubes were then placed in a shallow ice bath to ensure that the heavy organic phases become viscous enough to permit simple decantation of the upper light organic and aqueous phases. After decantation of the upper phases, each heavy organic phase was suspended in several mL of MIBK, combined into a separatory funnel, and sufficient MIBK added to provide a solution of less than 0.3 M. (Higher concentrations of DtBuCH18C6 increased the likelihood of emulsions.) The organic phase was subsequently washed with three volumes of 0.10 M HCl at an organic/aqueous phase ratio (O/A) of about 2, which stripped $SrCl_2$ from the organic extract. A final wash with $H_2O$ at 60° C. was performed to remove coextracted acid (elevated temperature suppressed the formation of emulsions), the aqueous phase was drained, and the MIBK was removed by rotary evaporation. Entrained $H_2O$ can result in an opaque product that can be removed using the toluene/$H_2O$ azeotrope.

Results using the procedure shown in FIG. 20 appropriately scaled to an 80 g batch of as-hydrogenated DtBuCH18C6 (Batch 592) are shown in FIG. 21. The top panel shows a rather complicated chromatogram indicating substantial quantities of a ring-substituted acyclic ether, (tBuB)(tBuCH)18C6, and a complicated distribution of DtBuCH18C6 convoluted with the ring-substituted acyclic butyl ether (see FIG. 21C). FIG. 21C shows the results of a small-scale purification using n-heptane as diluent and 1.25 M $SrCl_2$ in 4.5 M HCl as the aqueous phase. A 78.0 percent pure sample of DtBuCH18C6 was obtained in 59.3 percent yield, with less than 10 percent of each of the aforementioned cyclic and acyclic impurities. FIG. 21C shows the RPLC-MS chromatogram for the n-heptane light organic phase obtained from the 80 g purification, and it can be readily seen that this phase is enriched in the various impurities and substantially depleted of DtBuCH18C6. FIG. 21D shows the purity of the product obtained from the heavy organic phase, which has a DtBuCH18C6 content of 83.4 percent and is substantially enriched from the 60.2 percent untreated material.

Figure 21A:
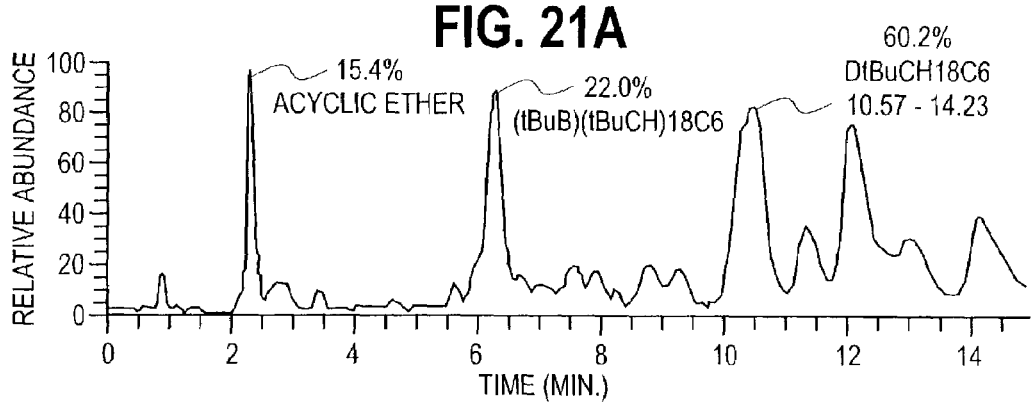
FIG. 21 in four panels shows RPLC-MS chromatograms of Batch 592 of DtBuCH18C6 extractant before (FIG. 21A) and after purification by third phase formation using n-heptane as diluent and 1.25 M SrCl$_2$ in 4.5 M HCl as the aqueous phase. Results are shown for a 2 gram purification (59.3% recovery.
FIG. 21B), and the light organic (FIG. 21C) and heavy organic (91.9% recovery; D$_{Sr}$=4.6.
FIG. 21D) phases after purification by third phase formation of an 80 g sample of DtBuCH18C6.
Figure 21B:
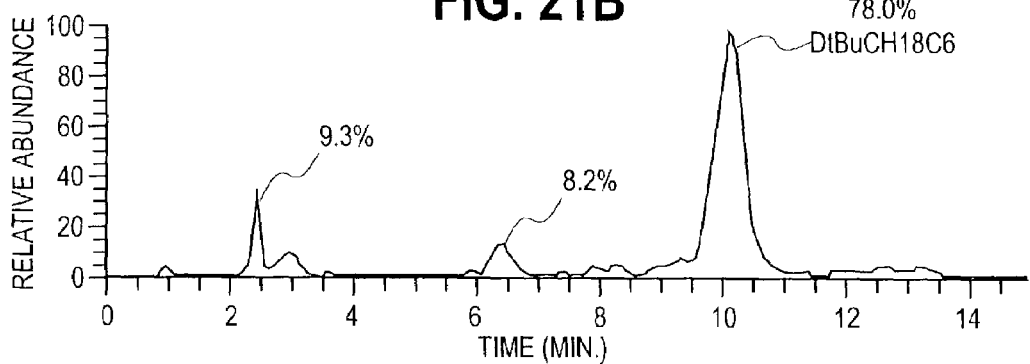
Figure 21C:
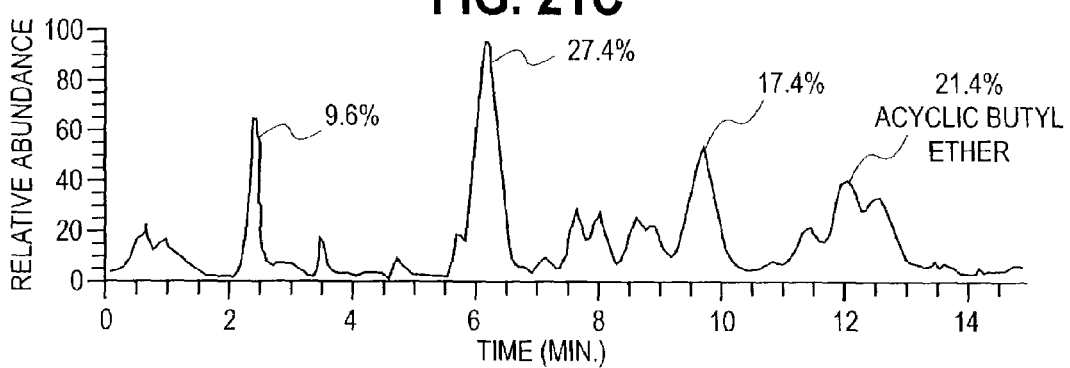
Figure 21D:
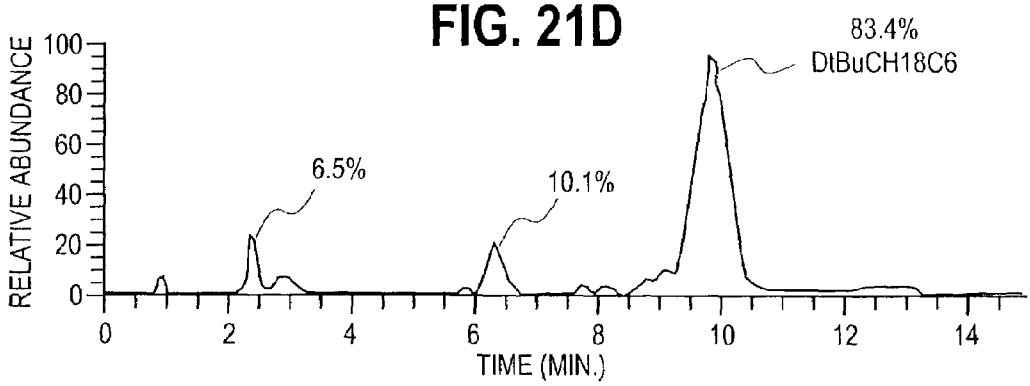

Also observed from these studies is the increase from $D_{Sr}$=2.6 for the untreated sample (FIG. 21A) to $D_{Sr}$=4.6 for the sample purified by third phase formation (FIG. 21D). As mentioned earlier, the yield of 59.3 percent obtained on the 2 g scale increased to 91.9 percent at the 80 g scale, and is further complemented by an increase in the DtBuCH18C6 purity of about 5 percent.

BEST MODE FOR CARRYING OUT THE INVENTION

All chemicals were of ACS reagent grade or better. All $H_2O$ was treated using a commercial deionization system.

Synthesis

The heterogeneous catalytic hydrogenation of DtBuB18C6 (Chemodynamics, L.P.) has been reported, [Gula et al., U.S. Pat. No. 5,478,953 (1995)] and this procedure was utilized here with only minor modifications. Reverse-phase high performance liquid chromatography coupled with mass spectrometric analysis (RPLC-MS) indicated significant differences in both the type and concentration of impurities in each batch of DtBuCH18C6, and such differences have largely been attributed to variations in the activity of the catalyst. As a result of such batch variations, samples of as-hydrogenated DtBuCH18C6 are referred to by their batch number.

Given that the DtBuCH18C6 content varies by batch and that the specific purification strategies discussed here generally involve the addition of substoichiometric quantities of $Sr^{2+}$, all yields are reported with respect to $Sr^{2+}$ as the limiting reactant used in the purification process, except where noted differently. This approach accounts for variations in the DtBuCH18C6 content by synthesis batch and also permits a comparison of yields between different purification methods.

Analysis

Thin layer chromatography (TLC) was used for qualitative determination of sample purity and also was used to screen samples prior to submission for RPLC-MS analysis. Silica gel TLC plates with an inorganic binder and 250 μm layer thickness (Analtech, Inc., Newark, Del.) were used with variable solvent compositions ranging from 2.5–7.5 percent (v/v) $CH_3OH$ in $CH_2Cl_2$. Band development was accomplished by chemical oxidation using an aqueous $H_2SO_4/(NH_4)_2MoO_4/Ce(SO_4)_2$ dip solution.

Preparative-scale TLC (PTLC) was used to separate the DtBuB18C6, (tBuB)(tBuCH)18C6, and DtBuCH18C6 in Batch 492 using 10 percent $CH_3OH$ in $CH_2Cl_2$ on silica gel PTLC plates having a 1000 μm layer thickness (Analtech, Inc., Newark, Del.). A preliminary PTLC separation was performed and three bands were chemically developed to serve as a template. A second PTLC separation was immediately performed and the three bands located using the distances from the template ($R_f$=0.65, 0.54, and 0.42). Each band was subsequently scraped from the glass support into a separate vial.

The crown ethers were extracted from the silica gel substrate by shaking for 10 minutes with 10 mL of 50 percent $CH_3OH$ in $CH_2Cl_2$. After permitting the solid substrate to settle, each supernatant was collected, another 5 mL of 50 percent $CH_3OH$ in $CH_2Cl_2$ was added, and the mixture was maintained for about 14 hours before the supernatant was again separated from the solid silica. After a final contact of the solid with 2 mL of 50 percent $CH_3OH$ in $CH_2Cl_2$, the three wash solutions for each sample (i.e., band) were combined, filtered, and the solvent removed by rotary evaporation to yield (by RPLC-MS) DtBuB18C6 as a white solid, (tBuB) (tBuCH)18C6 as a colorless oil, and DtBuCH18C6 as a colorless oil.

TLC as described before using 5 percent $CH_3OH$ in $CH_2Cl_2$ for the Batch 492 mixture formed three intense spots with $R_f$=0.20, 0.12, and 0.04. Each of the three bands scraped from the PTLC experiment exhibited only a single spot by TLC that was confirmed by RPLC-MS to be DtBuB18C6 with $R_f$=0.14, (tBuB) (tBuCH)18C6 with $R_f$=0.10, and DtBuCH18C6 with $R_f$=0.04.

The RPLC-MS analyses were performed by MediChem Research, Inc., using chromatographic conditions modified slightly from a previously published method. [Lasorkin et al., Zh. Anal. Khim. (1984) 39:1115 and Dietz et al., Sep. Sci. Technol. (1999) 34:2943–2956.] The protocol involved about 15 minutes of elution on a $C_{18}$-bonded reverse-phase silica gel column (LUNA-C18-2 column, 100×4.6 mm; (Phenomenex, Inc., Torrance, Calif.) using 20 percent $H_2O$/80 percent $CH_3CN$ as eluent.

Mass spectrometry utilized atmospheric pressure chemical ionization and an ion-trap mass detector was used for peak detection. The chromatograms were prepared using the total ion count from the mass spectrometer and a full mass spectrum for each time increment was recorded. No fragmentation of the polyethers was observed, and only the $H^+$ or $H_3O^+$ adducts of each polyether were observed in the mass spectra.

Retention times (RT) of the components vary with chromatographic conditions and the age of the column; however, the relative RT of the different components and the elution sequence remain fairly constant. The reproducibility of chromatographic peak integration (used to obtain the composition of mixtures) typically varied in the 2–4 percent range between identical samples, and peaks integrated at less than 5 percent are considered to be at the lower limit of statistical significance in these studies.

All distribution ratios were determined by first preequilibrating 2.5 mL of 0.10 M DtBuCH18C6 (as-received product or purified) in 1-octanol with 2.5 mL of 1.0 M $HNO_3$ and vortex mixing for about 2 minutes. After about 2 minutes of centrifugation, the aqueous phase was withdrawn and the preequilibration step was repeated. A 2.4 mL aliquot of fresh 1.0 M $HNO_3$ was then added along with 0.10 mL of 1000 ppm Sr standard solution in 1.0 M $HNO_3$. The phases were vortex mixed for about 2 minutes and followed by about 2 minutes of centrifugation to disengage the phases. The aqueous phase was withdrawn and diluted for analysis, whereas the concentration of Sr in the organic phase was calculated by difference. (As a check on this difference calculation, several studies were performed in which the organic extract was stripped three times with 2.0 mL of 0.05

M HNO$_3$ by vortex mixing and centrifuging as described above. All three of the strip raffinates were combined and diluted for analysis and yielded the same values for D$_{Sr}$ as obtained by the difference technique.) The distribution ratio is calculated as:

$$D_{Sr} = \frac{\text{(ppm } Sr \text{ in aqueous phase before contact} - \text{ppm } Sr \text{ in aqueous phase after contact)}}{\text{ppm } Sr \text{ in aqueous phase after contact}}$$

All distribution ratios were collected at 23($\pm$2)° C. and are accurate to $\pm$10 percent. Strontium analysis was accomplished using inductively coupled plasma-atomic emission spectroscopy on a Liberty Series II instrument (Varian, Inc., Mulgrave, Victoria Australia).

EXAMPLE 1

Purification by Precipitation of Metal Complex

A 1.96 g sample of as-hydrogenated DtBuCH18C6 Batch 512 (69.5 percent DtBuCH18C6) was diluted to 5 mL with ethylene glycol dimethyl ether (glyme) and dissolved by stirring at 65($\pm$2)° C. A 0.66 g quantity of SrCl$_2$.6H$_2$O was added and the mixture was stirred at $^{65}$($\pm$2)° C. for about 10 minutes to effect dissolution. The solution was stored at 8($\pm$1)° C. for about 45 minutes to induce precipitation of a white solid that was filtered, washed with a small quantity of cold glyme, collected, and dissolved in 10 mL CH$_3$OH. This solution was subsequently contacted with 1 mL of 1.0 M Na$_2$SO$_4$ in water and, after vigorous manual shaking, the solid SrSO$_4$ was settled by centrifugation. The SrSO$_4$ pellet was filtered and washed with more CH$_3$OH. Another 1 mL of 1.0 M Na$_2$SO$_4$ was added to the DtBuCH18C6-containing filtrate, the mixture was shaken, and then was centrifuged to settle the SrSO$_4$.

Residual solids were filtered away and 15 mL of methyl isobutyl ketone (MIBK) and 11 mL of H$_2$O were added to the filtrate to afford a two phase system that was vigorously shaken for about 2 minutes, centrifuged for about 2 minutes, and followed by removal of the aqueous phase. The organic phase was washed twice more with 10 mL aliquots of H$_2$O using the procedure described above. The MIBK was subsequently removed by rotary evaporation and the purified extractant was assayed by RPLC-MS (FIG. 6B).

EXAMPLE 2

Purification by Induced Precipitation of Metal Complex

A 25 g sample of DtBuCH18C6 Batch 585 (62.2 percent DtBuCH18C6) was dissolved in 100 mL isopropyl alcohol, after which 4.99 grams SrCl$_2$.6H$_2$O were added. The mixture was stirred for about 16 hours and only a small amount of suspended white solid was observed. The solid was compacted by centrifuging for 10 minutes and the supernatant was decanted and concentrated by rotary evaporation. Methyl t-butyl ether (MTBE, 100 mL) was added to the supernatant residue and thoroughly mixed to yield a white suspension that was divided into three aliquots that were each centrifuged for 15 minutes.

The supernatants were decanted away from the pellets and each pellet was resuspended in 20 mL MTBE, centrifuged, and the supernatants again decanted. This process was repeated twice more before each of the pellets was contacted with 20 mL MIBK and 2 mL H$_2$O. The aqueous phases were drained and combined. The MIBK phases were combined and extracted with 15 mL H$_2$O. This H$_2$O phase was added to the combined aqueous phases from the previous extractions to give a cloudy mixture that was subsequently extracted with 10 mL MIBK.

Figure 9B:
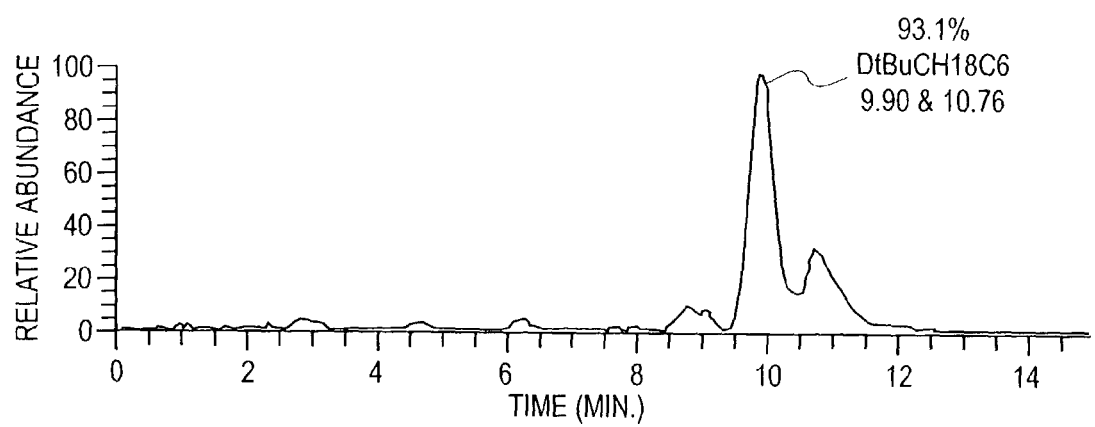

The resulting phases were clear, and this MIBK phase was added to the three combined MIBK phases from the previous extractions. This solution was contacted 8 times with 40 mL aliquots of H$_2$O to strip SrCl$_2$. The MIBK solvent was removed by rotary evaporation to yield 7.88 g of a highly viscous, colorless product that crystallized over several days at 23($\pm$2)° C. The resulting material was coated on an inert support to make an extraction chromatographic resin [Horwitz et al., *Anal. Chem.* (1991) 63:522–525] that exhibited a value of more than 100 free column volumes to peak maximum for elution of Sr$^{2+}$ in 3.1 M HNO$_3$, thereby confirming that this purification strategy produces a useful extraction chromatographic resin. The product obtained from a 2 g purification of Batch 585 using this procedure was assayed by RPLC-MS (FIG. 9B).

EXAMPLE 3

Purification by Solvent Extraction Third Phase Formation

A 2.01 g sample of untreated Batch 585 (62.2 percent DtBuCH18C6) was dissolved in 1.0 mL of toluene by gentle stirring at 65($\pm$2)° C. to provide a solution of about 1.4 M. A 2.4 mL aliquot of 0.9 M SrCl$_2$ in 3.0 M HCl (0.8:1 Sr$^{2+}$:DtBuCH18C6) was combined with the toluene solution and the phases were contacted by vigorous manual shaking for about 2 minutes. The mixture was centrifuged for about 2 minutes to disengage the three phases that formed.

The upper light organic and aqueous phases were withdrawn. The lower, viscous heavy organic phase was washed twice with about 1 mL of toluene prior to addition of 5 mL MIBK and 5 mL H$_2$O. The phases were contacted by shaking vigorously for about 2 minutes and disengaged by centrifugation for about 2 minutes.

The aqueous phase was withdrawn and another contact with 5 mL H$_2$O was similarly carried out. After the second aqueous strip solution was removed, a 5 mL aliquot of saturated Na$_2$SO$_4$ in H$_2$O was added (to ensure complete stripping of Sr$^{2+}$ from the organic phase) and contacted as described above. Another two contacts with 5 mL H$_2$O were carried out to remove any traces of Na$_2$SO$_4$ from the MIBK extract. After separating the aqueous phase, the MIBK was removed by rotary evaporation to yield 0.34 g, a portion of which was assayed by RPLC-MS (second panel of FIG. 14B).

All studies in which third phase formation was used to purify DtBuCH18C6 were performed using this same general procedure, except that the diluent, solute, or aqueous acidity was varied where noted. Any light organic phases that were assayed by RPLC-MS were subjected to the Sr$^{2+}$ stripping routine described above.

EXAMPLE 4

Purification of Calix[4]Arene by Solvent Extraction
Third Phase Formation

A 2 g sample of raw calix[4]arene is dissolved in several mL of a suitable diluent (e.g., chloroform, methylene chloride, toluene, etc.) to provide a reasonably concentrated solution (about 0.25–1.5 M). A 90 percent stoichiometric quantity of an ion-containing compound such as a metal salt (e.g., $Ca(NO_3)_2$, $SrCl_2$, $UO_2Cl_2$, and the like) in 3–6 M acid (e.g., HCl, $HNO_3$, etc.) is combined with the organic solution and the phases are contacted by vigorous shaking. The mixture is centrifuged to disengage the three phases and the light organic and aqueous phases are withdrawn.

The heavy organic phase is washed twice with a small volume of organic solvent prior to the addition of several mL of a diluent in which the purified calix[4]arene is soluble and that also is immiscible with $H_2O$ and easily distilled (e.g., toluene, nitrobenzene, and the like).

A comparable volume of $H_2O$ is added and the phases are vigorously contacted and disengaged by centrifugation. The aqueous phase is withdrawn and another aliquot of $H_2O$ is used for another extraction. After the second aqueous strip solution is removed, an aliquot of an $H_2O$-soluble stripping agent (e.g., $SO_4^{2-}$, ethylenediaminetetraacetate, etc.) is added to ensure complete stripping of the cation from the organic phase and contacted as described above. Another two contacts with aliquots of $H_2O$ are performed to remove any traces of stripping agent from the organic phase extract. After separating the aqueous phase, the diluent is removed by rotary evaporation to provide the purified calix[4]arene.

Each of the patents, applications and articles cited herein is incorporated by reference. The use of the article "a" or "an" is intended to include one or more.

From the foregoing it will be observed that numerous modifications and variations can be effectuated without departing from the true spirit and scope of the novel concepts of the invention. It is to be understood that no limitation with respect to the specific embodiment illustrated is intended or should be inferred. The disclosure is intended to cover by the appended claims all such modifications as fall within the scope of the claims.

What is claimed is:

1. A method for purifying a predetermined water-insoluble extractant selected from the group consisting of a macrocyclic polyether, acyclic polyether, polyamine, polythioether, a calixarene, a cryptand and a porphyrin from a composition containing one or more additional extractants, synthesis reaction starting materials and reaction byproducts that comprises the steps of:
    (a) providing a liquid phase composition containing said predetermined extractant and one or more additional extractants, synthesis reaction starting materials, and reaction byproducts that are dissolved as solutes in an organic diluent;
    (b) admixing an ion-containing compound with said composition to form an extractant/ion complex and a new phase, said extractant/ion complex having a greater affinity for said new phase than for said liquid phase, wherein if said ion also forms a further complex with said one or more additional extractants, synthesis reaction starting materials, and reaction byproducts that may be present in said composition, any such further complex formed exhibits less of an affinity for said new phase than does said predetermined extractant/ion complex;
    (c) separating said predetermined extractant/ion complex from said first named phase by using said new phase affinity;
    (d) separating said separated predetermined extractant/ion complex into extractant and ion; and
    (e) recovering said predetermined extractant.

2. The method according to claim 1 wherein said organic diluent is selected from the group consisting of a $C_1$–$C_5$ alcohol, a $C_3$–$C_9$ ketone, a $C_2$–$C_5$ ether, a poly($C_2$–$C_6$)ether, a $C_5$–$C_{14}$ straight chain alkane, a $C_5$–$C_{14}$ branched chain alkane, a $C_6$–$C_{12}$ aromatic solvent and a mixture thereof.

3. The method according to claim 1 wherein said ion-containing compound includes a cation selected from the group consisting of an ammonium ion, a potassium (I), a rubidium (I), a cesium (I), a silver (I), a thallium (I), a calcium (II), a strontium (II), a barium (II), a cadmium (II), a lead (II), a mercury (II), a scandium (III), a yttrium (III), a lanthanum (III), a lanthanide (III), and a bismuth (III) ion and mixtures thereof.

4. The method according to claim 1 wherein said new phase is a solid or liquid phase.

5. The method according to claim 1 wherein said predetermined extractant/ion complex exhibits a greater affinity for a solid phase than for said diluent.

6. The method according to claim 5 wherein said predetermined extractant/ion complex is separated from said diluent by precipitation of said complex.

7. The method according to claim 5 wherein said extractant/ion complex is separated from said diluent by direct precipitation of said complex.

8. The method according to claim 1 including the further step of recovering said predetermined extractant/ion complex prior to separating said ion and predetermined extractant.

9. The method according to claim 1 wherein said organic diluent is not miscible with water.

10. The method according to claim 9 wherein said ion-containing compound is admixed with said composition in the presence of water that comprises a second phase.

11. The method according to claim 10 wherein said predetermined extractant/ion complex forms a third phase.

12. The method according to claim 11 wherein said third phase is more dense than water.

13. The method according to claim 1 wherein said ion-containing compound is admixed as a solid with said composition.

14. A method for purifying a predetermined water-insoluble extractant selected from the group consisting of a macrocyclic polyether, acyclic polyether, polyamine, polythioether, a calixarene, a cryptand and a porphyrin from a composition containing one or more additional extractants, synthesis reaction starting materials and reaction byproducts that comprises the steps of:
    (a) providing a liquid phase composition containing said predetermined extractant and one or more additional extractants, synthesis reaction starting materials, and reaction byproducts that are dissolved as solutes in an organic diluent that is immiscible with water;
    (b) admixing an ion-containing compound with said composition in the presence of water to form an extractant/ion complex, a water phase, and a third phase, said extractant/ion complex having a greater affinity for said third phase than for said first-named phase, wherein if said ion also forms a further complex with said one or more additional extractants, synthesis reaction starting materials, and reaction byproducts that may be present in said composition, any such further complex formed exhibits less of an affinity for said new phase than does said predetermined extractant/ion complex;

(c) separating said predetermined extractant/ion complex from said diluent by using said third phase affinity;

(d) separating said separated predetermined extractant/ion complex into extractant and ion; and (e) recovering said predetermined extractant.

15. The method according to claim 14 wherein said organic diluent is selected from the group consisting of a $C_1$–$C_5$ alcohol, a $C_3$–$C_9$ ketone, a $C_2$–$C_6$ ether, a poly($C_2$–$C_6$)ether, a $C_5$–$C_{14}$ straight chain alkane, a $C_5$–$C_{14}$ branched chain alkane, a $C_6$–$C_{12}$ aromatic solvent and a mixture thereof.

16. The method according to claim 14 wherein said ion-containing compound includes a cation selected from the group consisting of an ammonium ion, a hydronium ion, a potassium (I), a rubidium (I), a cesium (I), a silver (I), a thallium (I), a calcium (II), a strontium (II), a barium (II), a cadmium (II), a lead (II), a mercury (II), a scandium (III), a yttrium (III), a lanthanum (III), a lanthanide (III), and a bismuth (III) ion and mixtures thereof.

17. The method according to claim 14 including the further step of recovering said third phase containing said extractant/ion complex prior to separating said ion and predetermined extractant.

18. The method according to claim 14 wherein said extractant is a macrocyclic polyether.

19. The method according to claim 14 wherein said new phase is more dense than water.

20. The method according to claim 14 wherein said ion-containing compound is dissolved in water when admixed with said composition.

21. The method according to claim 14 wherein said water present during said admixture contains about 0.5 to about 6 molar acid.

22. A method for purifying a predetermined water-insoluble macrocyclic polyether extractant from a composition containing one or more additional extractants, synthesis reaction starting materials and reaction byproducts that comprises the steps of:

(a) providing a liquid phase composition containing said macrocyclic polyether extractant and one or more additional extractants, synthesis reaction starting materials, and reaction byproducts that are dissolved as solutes in an organic diluent that is immiscible with water;

(b) admixing said composition with water that contains a dissolved strontium (II) ion-containing compound and about 0.5 to about 6 molar acid to form a macrocyclic polyether/ion complex, a water phase, and a third phase, said macrocyclic polyether/ion complex having a greater affinity for said third phase than for said first-named phase, wherein if said ion also forms a further complex with said one or more additional extractants, synthesis reaction starting materials, and reaction byproducts that may be present in said composition, any such further complex formed exhibits less of an affinity for said new phase than does said macrocyclic polyether/ion complex;

(c) separating said macrocyclic polyether extractant/ion complex from said diluent by using said third phase affinity;

(d) separating said separated predetermined extractant/ion complex into macrocyclic polyether extractant and ion; and (e) recovering said macrocyclic polyether extractant.

23. The method according to claim 22 wherein the water-immiscible organic diluent is a $C_6$–$C_{12}$ straight chain, branched chain or cyclic alkane or a $C_6$–$C_9$ aromatic solvent.

24. The method according to claim 22 wherein said water present during said admixture contains about 3 to about 5 molar acid.

25. The method according to claim 24 wherein said acid is hydrochloric, perchloric or nitric acid.

26. The method according to claim 22 wherein said macrocyclic polyether is a bis-ring-substituted macrocyclic polyether.

27. The method according to claim 26 wherein said bis-ring-substituted macrocyclic polyether is a di-($C_1$–$C_6$-alkyl-substituted)benzo-18-crown-6 or a di-($C_1$–$C_6$-alkyl-substituted) cyclohexano-18-crown-6.

28. The method according to claim 22 wherein organic diluent has a density that is less than that of water.

* * * * *